(12) United States Patent
Ozenberger et al.

(10) Patent No.: US 7,005,295 B1
(45) Date of Patent: Feb. 28, 2006

(54) β-AMYLOID PEPTIDE-BINDING PROTEINS AND POLYNUCLEOTIDES ENCODING THE SAME

(75) Inventors: Bradley A. Ozenberger, Newtown, PA (US); Jonathan A. Bard, Doylestown, PA (US); Eileen M. Kajkowski, Ringoes, NJ (US); Jack S. Jacobsen, Ramsey, NJ (US); Stephen G. Walker, East Windsor, NJ (US); Heidi Sofia, Walla Walla, WA (US)

(73) Assignee: Wyeth, Madison, NJ (US)

(*) Notice: Subject to any disclaimer, the term of this patent is extended or adjusted under 35 U.S.C. 154(b) by 512 days.

(21) Appl. No.: 09/774,936

(22) Filed: Jan. 31, 2001

Related U.S. Application Data

(63) Continuation of application No. 09/172,990, filed on Oct. 14, 1998, now abandoned, which is a continuation-in-part of application No. 09/060,609, filed on Apr. 15, 1998, now abandoned.

(60) Provisional application No. 60/064,583, filed on Apr. 16, 1997.

(51) Int. Cl.
*C07H 21/02* (2006.01)
*C07H 21/04* (2006.01)
*C12N 5/10* (2006.01)
*C12N 15/63* (2006.01)

(52) U.S. Cl. .................. 435/320.1; 435/325; 536/23.5; 536/24.3; 536/24.31; 536/24.33

(58) Field of Classification Search ............... 536/23.5, 536/24.3, 24.31, 24.33; 435/69.1, 325, 320.1
See application file for complete search history.

(56) References Cited

U.S. PATENT DOCUMENTS

| | | | |
|---|---|---|---|
| 4,518,584 | A | 5/1985 | Mark et al. |
| 4,987,071 | A | 1/1991 | Cech et al. |
| 5,116,742 | A | 5/1992 | Cech et al. |
| 5,652,092 | A | 7/1997 | Vitek et al. |
| 5,656,477 | A | 8/1997 | Vitek et al. |
| 5,693,478 | A | 12/1997 | Vitek et al. |

FOREIGN PATENT DOCUMENTS

| | | |
|---|---|---|
| WO | WO 88/03951 | 6/1988 |
| WO | WO 90/08832 | 8/1990 |
| WO | WO 95/34646 | 12/1995 |
| WO | WO 96/13513 | 5/1996 |
| WO | WO 96/25435 | 8/1996 |
| WO | WO 98/46636 | 10/1998 |
| WO | WO 99/24836 | 5/1999 |
| WO | WO 99/31969 | 7/1999 |
| WO | WO 99/46289 | 9/1999 |
| WO | WO 00/22125 | 4/2000 |

OTHER PUBLICATIONS

Rudinger. In *Peptide Hormones*, J. A. Parsons, editor. University Park Press, Baltimore, 1976.*
Bonaldo et al. *Genome Res.*, vol. 6, pp. 791-806, 1996.*
J. Biol. Chem., "Modulation of GDP Release from Transducin by the Conserved $Glu^{134}Arg^{135}$ Sequence in Rhodopsin", S. Acharya et al., 271, No. 41, (Oct. 1996) pp. 25406-25411.
J. Mol. Biol., "Basic Local Alignment Search Tool", S.F. Altschul et al., (1990) 215, pp. 403-410.
Lett. Nature, "Mutations in the channel domain alter desensitization of a neuronal nicotinic receptor", F. Revah et al., 353, (Oct. 1991), pp. 846-.
Nature, "RAGE and Amyloid-β-peptide neurotoxicity in Alzheimer's disease", Shi Du Yan et al., 382, (Aug. 1996) pp. 685-691.
Nature, "Scavenger receptor-mediated adhesion of microglia to β-amyloid fibrils", J. El Khoury et al., 382 (Aug. 1996), pp. 716-719.
Nature, "Segregation of a missense mutation in the amyloid precursor protein gene with familial Alzheimer's disease", 349 (Feb. 1991), pp. 704-706.
Nature Genetics, "Presenile dementia and cerebral haemorrhage linked to a mutation at codon 692 of the β-amyloid precursor protein gene", L. Hendriks et al., 1 (Jun. 1992), pp. 218-221.
Neurobiology of Aging, "A novel species-specific RNA related to alternatively spliced amyloid precursor protein mRNAs", J.S. Jacobsen et al., 12, (1991) pp. 575-583.
J. Biol. Chem., "The release of Alzheimer's disease β amyloid peptide is reduced by phorbol treatment", J.S. Jacobsen et al., 269, No. 11 (Mar. 1994), pp. 8376-8382.
Mol. Cell. Biol., "Effects of expression of mammalian Gα and hybrid mammalian yeast Gα proteins on the yeast pheromone response signal transduction pathway", Yoon-Se Kang et al., 10, No. 6 (Jun. 1990), pp. 2582-2590.
Nat. Genetics, "The Alzheimer's Aβ peptide induces neurodegeneration nd apoptotic cell death in transgenic mice", 9, (Jan. 1995), pp. 21-30.
A. Neuropathol., "Cell death in Alzheimer's disease evaluated by DNA fragmentation in situ", H. Lassman et al., 89 (Springer-Vertaag 1995), pp. 35-41.

(Continued)

*Primary Examiner*—Brenda Brumback
*Assistant Examiner*—Stephen Gucker
(74) *Attorney, Agent, or Firm*—Nixon Peabody LLP; Raymond Van Dyke

(57) ABSTRACT

Novel proteins which bind human β-amyloid peptide, polynucleotides which encode these proteins, and methods for producing these proteins are provided. Diagnostic, therapeutic, and screening methods employing the polynucleotides and polypeptides of the present invention are also provided.

30 Claims, 10 Drawing Sheets

OTHER PUBLICATIONS

Science, "Mutation of the Alzheimer's disease amyloid gene in hereditary cerebral hemorrhage, Dutch type", 243, (Jun. 1990), pp. 1124-1126.

Neurobiology, "Apoptosis is induced by β-amyloid in cultured central nervous system neurons", D.T. Loo et al., 90, (Sep. 1993), pp. 7951-7955.

Med. Sciences, "Reversible in vitro growth of Alzheimer disease β-amyloid plaques by deposition of labeled amyloid peptide", J.E. Maggio et al., 89 (Jun. 1992), pp. 5462-5466.

Nat. Genetics, "A pathogenic mutation for probable Alzheimer's disease in the APP gene at the N-terminus of β-amyloid", M. Mullan et al., 1 (Aug. 1992), pp. 345-347.

Sci., "A mutation in the amyloid precursor protein associated with hereditary Alzheimer's disease", J. Murrell et al., 254 (Oct. 1991), pp. 97-99.

Lett. Nat., "Alzheimer amyloid protein precursor complexes with brain GTP-binding protein $G_o$", I. Nishimoto et al., 362 (Mar. 1993), pp. 75-79.

Nat. Medicine, "Secreted amyloid β-protein similar to that in the senile plaques of Alzheimer's disease is increased in vivo by the presenilin 1 and 2 and APP mutations linked to familial Alzheimer's disease", D. Scheuner et al., 2 No. 8 (Aug. 1996), pp. 864-870.

Neurosci., "Alzheimer's Disease: Genotypes, Phenotype, and Treatments",D.J. Selkoe, 275 (Jan. 1997), pp. 630-631.

J. Neurosci., "Voltage-gated $K^+$ channel β subunits: Expression and distribution of Kvβ1 and Kvβ2 in adult rat brain", K.J. Rhodes et al., 16 (Aug. 1996), pp. 4846-4860.

Mol. Endo., "Functional interaction of ligands and receptors of the hematopoietic superfamily in yeast", B.A. Ozenberger et al., 9 No. 10 (1995), pp. 1321-1329.

Exp. Neurology, "Evidence of apoptotic cell death in Alzheimer's disease", G. Smale et al., 133 (1995), pp. 225-230.

Sci., "Amyloid β protein gene: cDNA, mRNA distribution and genetic linkage near the Alzheimer locus", (Jan. 1987), pp. 880-884.

Proc. Natl. Acad. Sci., "Detection of conserved segments in proteins: Iterative scanning of sequence databases with alignment blocks",R.L. Tatusov et al., 91 (Dec. 1994), pp. 12091-12095.

Cell, "The p21 Cdk-interacting protein Cip 1 is a potent inhibitor of G1 cyclin-dependent kinases", J. Wade Harper et al., 75 (Nov. 1993), pp. 805-816.

Elsevier Sci., "Ultrastructural analysis of β-amyloid-induced apoptosis in cultured hippocampal neurons", J.A. Watt et al., 661 (1994), pp. 147-156.

Sci., "G-protein-mediated neuronal DNA fragmentation induced by familial Alzheimer's disease-associated mutants of APP", T. Yamatsuji et al., 272 (May 1996), pp. 1349-1352.

Nature, "An intracellular protein that binds amyloid-β peptide and mediates neurotoxicity in Alzheimer's disease", Shi Du Yan et al., 389 (Oct. 1997), pp. 689-.

Science, Lewin, 237 (1987), p. 1570.

Biotech Adv., Gellissen et al., 10 (1992), pp. 179-189.

Nature, Adams et al., 377 (1995), pp. 3-174.

Genbank Accession No. AA306979, Adams et al., 1995.

Glossary of Genetics and Cytogenetics, Rieger et al., 1976, pp. 17-18.

Journal of Cell Biology, Burgess et al., 111 (1990), pp. 2129-2138.

Molecular and Cellular Biology, Lazar et al., 8(3) (Mar. 1988), pp. 1247-1252.

"Peptide Hormones," Rudinger, University Park Press, Jun. 1976, pp. 1-7.

"Molecular Cloning," Sambrook et al., Second Edition, Cold Spring Harbor Laboratory Press, 1989, pp. 17.1-17.44.

Database EMBL—EMEST7 'Online! Entry/Acc.No. Al143226, Sep. 29, 1998 Strausberg, R., "qb76e01.x1 Soares_fetal_heart_NbHH19W *Homo sapiens* cDNA clone Image:1706040 3' similar to WP:C02F5.3 CE00039 GTP-Binding Protein; mRNA sequence." XP002135394.

Database EMBL—EMEST1 'Online! Entry/Acc.No. AA628537, Oct. 28, 1997 Hillier, L., et al., "af27h04.s1 Soares total fetus Nb2HF8 9w *Homo sapiens* cDNA clone 1032919 3' similar to WP:C02F5.3 CE00039 GTP-Binding Protein;." XP002135395.

Database EMBL—EMEST3 'Online! Entry/Acc.No. AA772225, Jan. 31, 1998 Strausberg, R., et al., "ai41c01.s1 Soares_parathyroid_tumor_NbHPA*Homo sapiens* cDNA clone 1359552 3' similar to WP:C02F5.3 CE00039 GTP-Binding Protein; mRNA" XP002135396.

Proc. Nat'l. Acad. Sci. USA, "Expression, stability, and membrane integration of truncation mutants of bovine rhodopsin," Heymann, J.A.W., et al., 94 (1997), pp. 4966-4971.

FASEB Journal, "A novel family of apoptosis modulators contain a G protein coupling motif," Kajkowski, E., et al., 13 (1999), pp. A1434-Abstr. 589.

Database EMBL Nucleotide and Protein Sequences, May 10, 1996, XP002081589 Hinxton, GB, AC=W29859. Soares mouse p3NMF 19.5 *Mus musculus* cDNA clone 348008 5', similar to GTP-Binding Protein.

The Journal of Biological Chemistry, "Arrest of beta-amyloid fibril formation by a peptapeptide ligand," Tjernberg, L.O., et al., 271 (1996), pp. 8545-8548.

Database EMBL Nucleotide and Protein Sequences, Jul. 22, 1998, XP002081601 Hinxton, GB, AC=Al057115. Soares total fetus Nb2HF8 9w *Homo sapiens* cDNA clone, similar to GTP-binding protein. Spans from nt 3260632; Spans from aa residues 1-101.

Ausubel, F.M. et al. (eds), "Current Protocols in Molecular Biology," *John Wiley & Sons, Inc.*, Sections 2.10 and 6.3-6.4 (1995).

Kajkowski, E.M. et al., β-Amyloid peptide-induced apoptosis regulated by a novel protein containing a G protein activation module, *J. Biol. Chem.*, 276(22):18748-56 (2001).

Kaufman, R.J. et al., Improved vectors for stable expression of foreign genes in mammalian cells by use of the untranslated leader sequence from EMC virus, *Nucleic Acids Res.* 19(16):4485-90 (1991).

Kaufman, R.J., Selection and coamplification of heterologous genes in mammalian cells, *Methods Enzymol.*, 185:537-66 (1990).

Kyte, J. and Doolittle, R.F., A simple method for displaying the hydropathic character of a protein, *J. Mol. Biol.*, 157(1): 105-32 (1982).

Summers, M D. and Smith, G E., A manual of methods for baculovirus vectors and insect cell culture procedures, *Texas Agricultural Experiment Station Bulletin*, 1555 College Station, Texas, Texas A&M University; (1987).

Bartel, D.P. and Szostak, J.W., Isolation of new ribozymes from a large pool of random sequences, *Science*, 261:1411-1418, (1993).

Bradley, F. et al., Formation of germ-line chimaeras from embryo-derived teratocarcinoma cell lines, *Nature* 309:225-256 (1984).

Evans, M.J. and Kaufman, M.H., Establishment in culture of pluripotential cells from mouse embryos, *Nature* 292:154-156 (1981).

Fields, S. and Song, O.-K., A novel genetic system to detect protein-protein interactions, *Nature*, 3240:245-246 (1989).

Gaultier, C. et al., α-DNA. IV: α-anomeric and β-anomeric tetrathymidyiates covalently linked to intercalating oxazolopyridocarbazole, synthesis, physicochemical properties and poly (rA) binding, *Nucl. Acids Res.,* 15: 6625-6641 (1987).

Gossler, A. et al., Transgenesis by means of blastocyst-derived embryonic stem cell lines, *Proc. Natl. Acad. Aci. USA,* 83(23):9065-9069 (1986).

Haselhoff, J. and Gerlach, W.L., Simple RNA enzymes with new and highly specific endoribonuclease activities, *Nature,* 334(6183):585-91 (1988).

Helene, C. et al., Control of gene expression by triple helix-forming oligonucleotides, The Antigene Strategy, Ann. N. Y. Acad. Sci., 660:27-36 (1992).

Helene, C., The anti-gene strategy: control of gene expression by triplex-forming-oligonucleotides, *Anticancer Drug Des.,* 6(6):569-84 (1991).

Inoue, H. et al., Sequence-dependent hydrolysis of RNA using modified oligonucleotide splints and RNase H, *FEBS Lett.,* 215(2):327-30 (1987).

Inoue, H. et al., Synthesis and hybridization studies on two complementary nona(2'-O-methyl)ribonucleotides, *Nucl. Acids Res.,* 15:6131-6148 (1987).

Jahner, D. et al., Insertion of the bacterial gpt gene into the germ line of mice by retroviral infection, *Proc. Natl. Acad. Sci. U S A,* 82(20):6927-31 (1985).

Lewin, B., Genes II, John Wiley & Sons, NY, p. 96 (1985).

Maher, L.J., III, DNA triple-helix formation: an approach to artificial gene repressors?, *Bioessays,* 14(12):807-15 (1992).

Brinster, R.L. et al., Factors affecting the efficiency of introducing foreign DNA into mice by microinjecting eggs, *Proc. Natl. Acad. Sci. U S A,* 82(13):4438-42 (1985).

Cole, S.P.C. et al., The EBV-hybridoma technique and its application to human lung cancer, in *Monoclonal Antibodies and Cancer Therapy,* vol. 27, UCLA Symposia on Molecular and Cellular Biology, New Series, R.A. Reisfeld and S.Sell (eds), pp. 77-96, Alan R. Liss, Inc., N.Y. (1985).

Haskell, R.E. and Bowen, R.A., Efficient production of transgenic cattle by retroviral infection of early embryos, *Mol. Reprod. Dev.,* 40(3):386-90 (1995).

Hogan, B. et al., Manipulating the Mouse Embryo, A Laboratory Manual, Cold Spring Harbor Press, Cold Spring Harbor, NewYork (1986).

Jaenisch, R., Germ line integration and Mendelian transmission of the exogenous Moloney leukemia virus, *Proc. Natl. Acad. Sci. U S A,* 73(4):1260-4 (1976).

Jaenisch, R., Transgenic animals, *Science,* 240(4858):1468-74 (1988).

Jahner, D. et al., De novo methylation and expression of retroviral genomes during mouse embryogenesis, *Nature,* 298:623-628 (1982).

Kohler, G. and Milstein, C., Continuous cultures of fused cells secreting antibody of predefined specificity, *Nature,* 256(5517):495-7(1975).

Kozbor, D and Roder, J.C., The production of monoclonal antibodies from human lymphocytes, *Immunology Today,* 4(3):72-79 (1983).

O'Brien, S.J. et al., Anchored reference loci for comparative genome mapping in mammals, *Nat Genet.,* 3(2):103-12 (1993).

O'Brien, S.J. et al., Mammalian genome organization: an evolutionary view, *Annu. Rev. Genet.,* 22:323-51 (1988).

Robertson, E. et al., Germ-line transmission of genes introduced into cultured pluripotential cells by retroviral vector. *Nature,* 323(6087):445-8 (1986).

Stewart, C. L. et al., Expression of retroviral vectors in transgenic mice obtained by embryo infection, *EMBO J.,* 6(2):383-8 (1987).

Van Der Putten, H. et al., Efficient insertion of genes into the mouse germ line via retroviral vectors, *Proc. Natl. Acad. Sci. U S A,* 82(18):6148-52 (1985).

Carver, E.A. and Stubbs, L., Zooming in on the human-mouse comparative map: genome conservation reexamined on a high-resolution scale, *Genome Res.,* 7(12):1123-37 (1997).

Johansson, M. et al., Comparative mapping reveals extensive linkage conservation—but with gene order rearrangements—between the pig and the human genomes, *Genomics,* 25(3):682-90 (1995).

Lyons, L.A. et al., Comparative anchor tagged sequences (CATS) for integrative mapping of mammalian genomes, *Nat. Genet.,* 15(1):47-56 (1997).

O'Brien, S.J. et al., Comparative genomics: lessons from cats, *Trends Genet.,* 13(10):393-9 (1997).

Sambrook, J., Fritsch, E.F., and Maniatis, T. (eds), "Molecular Cloning: A Laboratory Manual," Cold Spring Harbor Laboratory Press, Cold Spring Harbor, NY, *Chapters 9 and 11* (1989).

Krishnamurthy, K. et al., Characterization of fibrillogenesis of amyloid peptide, Abstracts of the American Chemical Society, Vol. , p. , 215th National Meeting and Exposition, Mar. 29-Apr. 2, 1998, Dallas, Texas.

Andrews, P. W. et al., Retinoic acid induces neuronal differentiation of a cloned human embryonal carcinoma cell line in vitro, *Dev. Biol.,* 103:285-293 (1984).

Cotman, C. W. and Anderson, A.J., A potential role for apoptosis in neurodegeneration and Alzheimer's disease, *Mol. Neurobiol.,* 10(1):19-45 (1995).

Burstein, E. et al., The second intracellular loop of the m5 muscarinic receptor is the switch which enables G-protein coupling, *J. Biol. Chem.,* 273:25422-24327 (1998).

Rosenthal, W. et al., Nephrogenic diabetes insipidus. A V2 vasopressin receptor unable to stimulate adenylyl cyclase, *J. Biol. Chem.,* 268:13030-13033 (1993).

Jones, P. et al., The function of a highly-conserved arginine residue in activation of the muscarinic M1 receptor, *Eur. J. Pharmacol.,* 288:251-257 (1995).

* cited by examiner

A  BBP-1

B  APP

US 7,005,295 B1

β-AMYLOID PEPTIDE-BINDING PROTEINS AND POLYNUCLEOTIDES ENCODING THE SAME

This application is a continuation of U.S. Ser. No. 09/172,990 filed Oct. 14, 1998, now abandoned, which is a continuation-in-part of U.S. Ser. No. 09/060,609 filed Apr. 15, 1998, now abandoned, which claims benefit of U.S. Provisional Application 60/064,583, filed Apr. 16, 1997, the contents of which are incorporated into this application by reference.

FIELD OF THE INVENTION

The present invention relates to a novel polynucleotides and proteins encoded by such polynucleotides, along with therapeutic, diagnostic, and research utilities for these polynucleotides and proteins. In particular, the invention relates to polynucleotides and proteins encoded by such polynucleotides which bind to β-amyloid peptide, one of the primary components of amyloid deposits associated with Alzheimer's Disease.

BACKGROUND OF THE INVENTION

Alzheimer's disease (AD) is a progressive dementing disorder of the elderly characterized by a series of structural abnormalities of the brain. Neurons in multiple regions of the central nervous system (CNS) become dysfunctional and die, resulting in alterations in synaptic inputs. Cell bodies and proximal dendrites of these vulnerable neurons contain neurofibrillary tangles composed of paired helical filaments, the main component of which is a phosphorylated microtubular-binding protein, namely tau. One of the hallmarks of the disease is the accumulation of amyloid containing deposits within the brain called senile (or neuritic) plaques. The principal component of amyloid plaques is β-amyloid peptide (hereinafter "BAP", also referred in the literature as Aβ, βAP, etc.) which forms dense aggregates during the course of AD.

BAP is a 39–43 amino acid peptide derived by proteolytic cleavage of amyloid precursor protein (hereinafter "APP") and composed of a portion of the transmembrane domain and the luminal/extracellular domain of APP. It is thought that the BAP peptide comprising 42 amino acids (BAP42) is potentially the more toxic aggregated form in humans. APP occurs as several BAP-containing isoforms. The major forms are comprised of 695, 751, and 770 amino acids, with the latter two APP containing a domain that shares structural and functional homologies with Kunitz serine protease inhibitors. In normal individuals, BAP does not accumulate and is rapidly removed from circulating fluids. However, the peptide can form plaques on surfaces of dystrophic dendrites and axons, microglia, and reactive astrocytes. The aggregation and deposition of BAP in neuritic plaques is postulated as one of the initiating events of AD. Investigation of the events leading to the expression and consequences of BAP and their individual roles in AD is a major focus of neuroscience research. In particular, the discovery of proteins that bind BAP is critical to advance understanding of the pathogenesis of the disease and to potentially introduce novel therapeutic targets.

Until the present invention, proteins and fragments thereof which bind with human BAP and which may be involved in the biological effects of BAP in AD had not been identified.

SUMMARY OF THE INVENTION

This invention provides novel isolated polynucleotides which encode gene products that selectively bind human β-amyloid peptide (BAP) amino acid sequences.

In one embodiment, the present invention provides a composition comprising an isolated polynucleotide selected from the group consisting of:
  (a) polynucleotide comprising the nucleotide sequence of SEQ ID NO: 1;
  (b) a polynucleotide comprising the nucleotide sequence of a β-amyloid peptide-binding protein (BBP) of clone BBP1-fl deposited under accession number ATCC 98617;
  (c) a polynucleotide encoding a β-amyloid peptide-binding protein (BBP) encoded by the cDNA insert of clone BBP1-fl deposited under accession number ATCC 98617;
  (d) a polynucleotide comprising the nucleotide sequence of SEQ ID NO: 1 from nucleotide 202 to nucleotide 807;
  (e) a polynucleotide comprising the nucleotide sequence of a β-amyloid peptide-binding protein (BBP) of clone pEK196 deposited under accession number ATCC 98399;
  (f) a polynucleotide encoding a β-amyloid peptide-binding protein (BBP) encoded by the cDNA insert of clone pEK196 deposited under accession number ATCC 98399;
  (g) a polynucleotide encoding a protein comprising the amino acid sequence of SEQ ID NO: 2;
  (h) a polynucleotide encoding a protein comprising a fragment of the amino acid sequence of SEQ ID NO: 2 having human β-amyloid peptide binding activity, the fragment comprising the amino acid sequence from amino acid 68 to amino acid 269 of SEQ ID NO: 2;
  (j) a polynucleotide which is an allelic variant of the polynucleotide of (a)–(f) above;
  (k) a polynucleotide which encodes a species homologue of the protein of (g)–(i) above; and
  (l) a polynucleotide capable of hybridizing under stringent conditions to any one of the polynucleotides specified in (a)–(h).

Preferably such polynucleotide comprises the nucleotide sequence of SEQ ID NO: 1; the nucleotide sequence of a β-amyloid peptide-binding protein (BBP) of clone BBP1-fl deposited under accession number ATCC 98617; or a polynucleotide encoding a β-amyloid peptide-binding protein (BBP) encoded by the cDNA insert of clone BBP1-fl deposited under accession number ATCC 98617. Another embodiment provides the gene corresponding to the cDNA sequence of SEQ ID NO: 1.

In other embodiments, the present invention provides a composition comprising a protein, wherein said protein comprises an amino acid sequence selected from the group consisting of:
  (a) the amino acid sequence of SEQ ID NO: 2;
  (b) the amino acid sequence of SEQ ID NO: 2 from amino acid 68 to amino acid 269;
  (c) the amino acid sequence encoded by the cDNA insert of clone BBP1-fl deposited under accession number ATCC 98617; and
  (d) fragments of the amino acid sequence of SEQ ID NO: 2 comprising the amino acid sequence from amino acid 185 to amino acid 217 of SEQ ID NO: 2.

Preferably such protein comprises the amino acid sequence of SEQ ID NO: 2 or the amino acid sequence of SEQ ID NO: 2 from amino acid 68 to amino acid 269. Fusion proteins are also claimed in the present invention.

In certain preferred embodiments, the polynucleotide is operably linked to an expression control sequence. The invention also provides a host cell, including bacterial, yeast, insect, and mammalian cells, transformed with such polynucleotides compositions.

Processes are also provided for producing a BBP which comprises (a) growing a culture of the host cell of claim 3 in a suitable culture medium; and (b) purifying the protein from the culture medium.

Compositions comprising an antibody which specifically reacts with such BBPs are also provided by the present invention.

Methods and diagnostic processes are provided for detecting a disease state characterized by the aberrant expression of human BAP, as well as methods for identifying compounds which regulate the activity of BBPs.

Another embodiment of the invention includes transgenic animals comprising a polynucleotide encoding a BBP operably linked to an expression control sequence.

BRIEF DESCRIPTION OF THE DRAWINGS

The following drawings depict certain embodiments of the invention. They are illustrative only and do not limit the invention otherwise disclosed herein.

expression plasmids. Samples were treated with BAP at the indicted concentrations for 44 hrs. Cells were prepared for determinations of nuclear morphology as described. Values represent percent-condensed nuclei of transfected cells (EGFP+). The differences between values for BBP1 samples versus controls at 2 or 8 µM BAP are highly significant (P<0.005) as determined by a Yates modified chi-square test of probability.

DETAILED DESCRIPTION OF THE INVENTION

Figure 5:
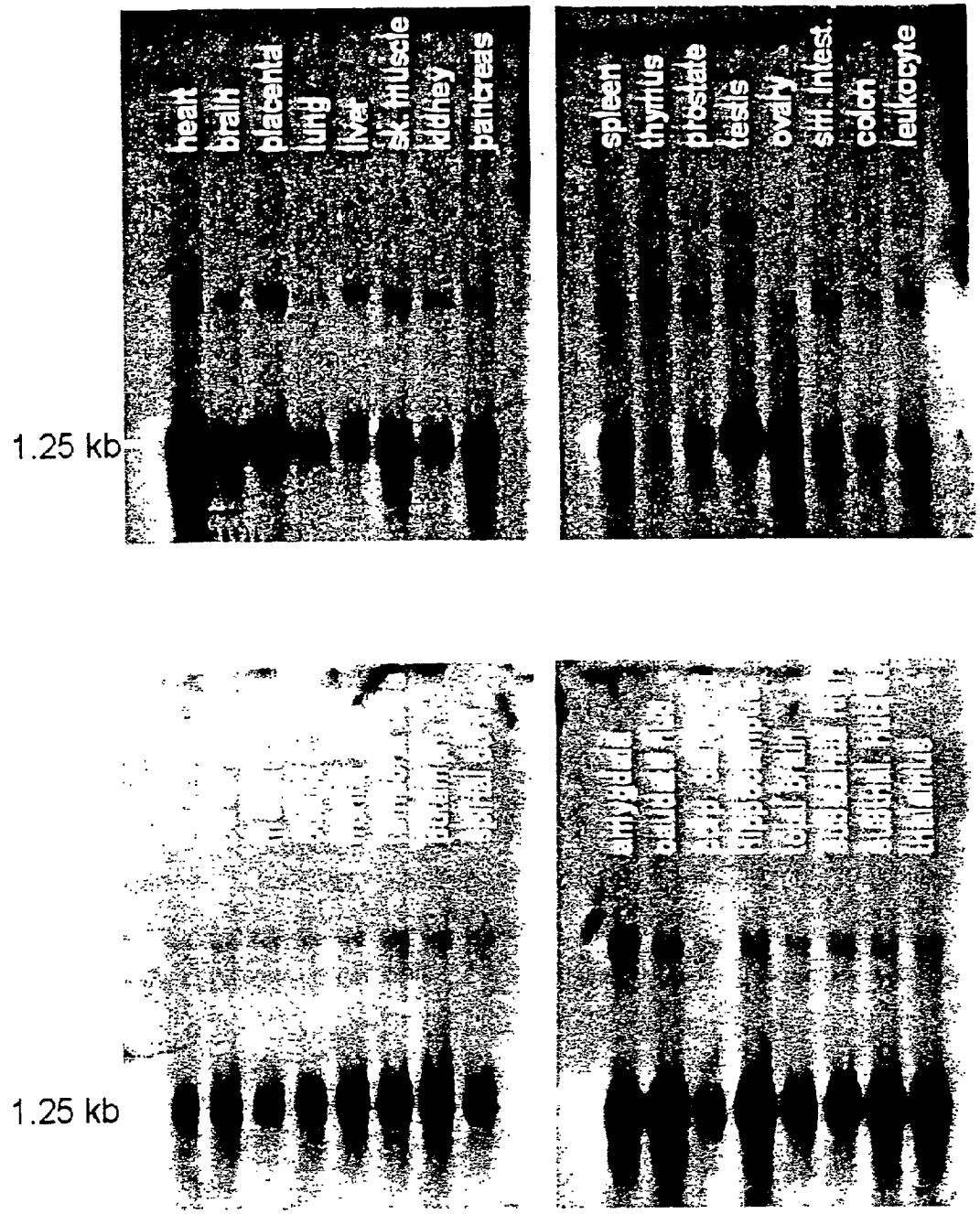
FIG. 5: Expression of BBP1 mRNA in human tissues (A) and brain regions (B). Nylon membranes blotted with 2 μg size fractionated poly-A RNA isolated from the indicated tissues were obtained from CLONTECH. These were hybridized with a radiolabeled BBP1 cDNA probe as described. A predominant band corresponding to 1.25 kb (determined from molecular weight markers, not shown) was observed in all lanes. Higher molecular weight bands likely correspond to heteronuclear RNA; the BBP1 gene contains several introns. Blots were stripped and reprobed with β-actin as a loading and RNA integrity control; all lanes exhibited equivalent signal (data not shown).

The present invention relates to the isolation and cloning of a human α-amyloid peptide binding protein (BBP1). BBP1 has been characterized as a fusion protein in a yeast 2 hybrid assay as binding to BAP, specifically the 42 amino acid fragment of BAP (BAP42). Expression of BBP1 has been shown in human tissues and in specific brain regions (FIG. 5). Importantly BBP1 has been demonstrated to selectively bind human BAP in a yeast 2 hybrid system as compared to rodent BAP. These findings support the premise that the BBP1 of the present invention may be used in the diagnosis and treatment of Alzheimer's Disease.

The BBP1 Coding Sequence

Figure 1:
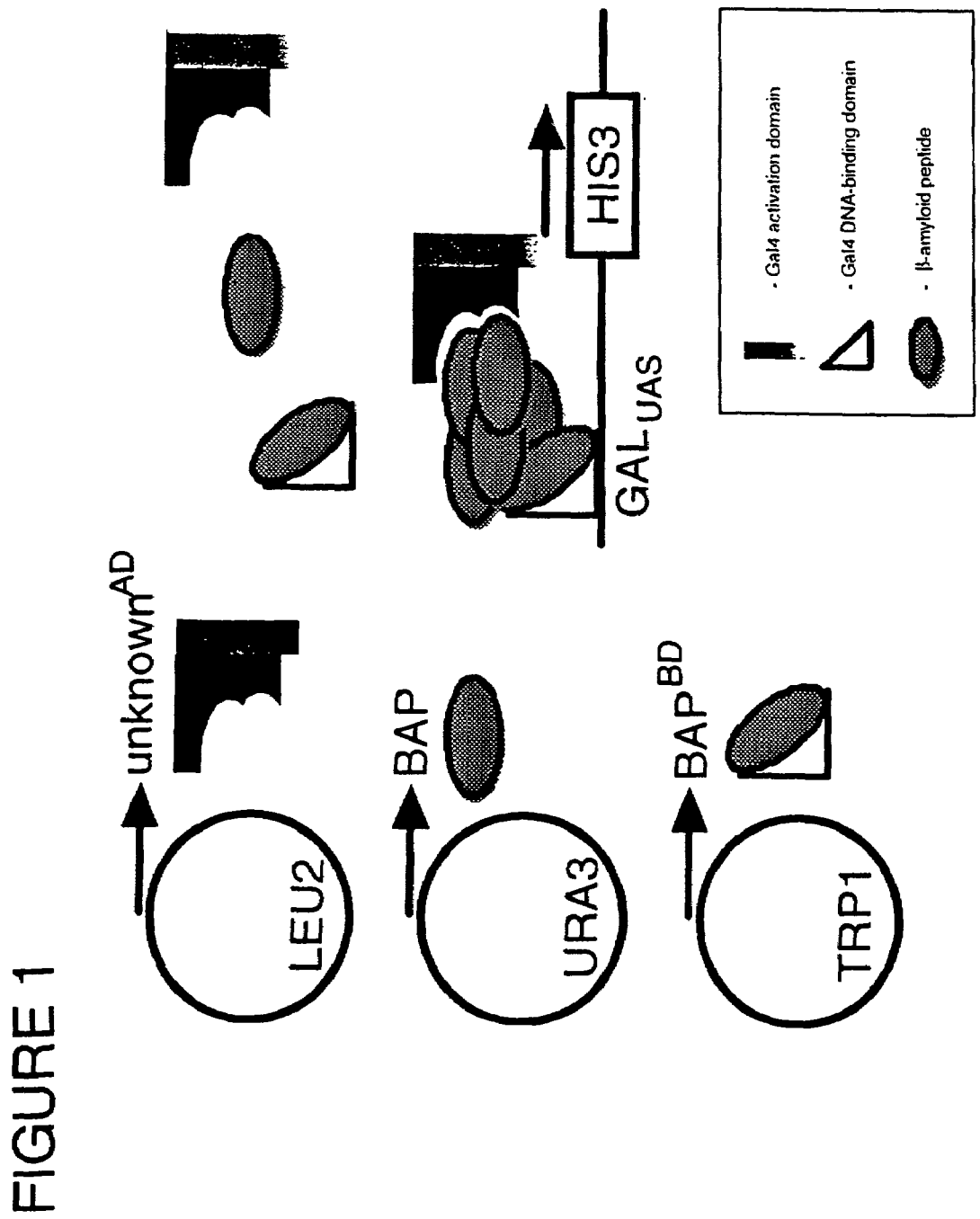
FIG. 1: Yeast 2-hybrid screen design. A Y2H host strain expressing the Gal4 DNA-binding domain fused to $BAP_{42}$ ($BAP^{BD}$; plasmid containing TRP1 marker) and nonfusion $BAP_{42}$ (BAP; plasmid containing URA3 marker) was transformed with a Y2H human fetal brain cDNA library (plasmid containing LEU2 marker) expressing Gal4 activation domain fusion proteins (unknown$^{AD}$) as described. Therefore, strains contained three episomal plasmids, denoted by circles, expressing the indicated protein. Positive protein—protein interactions reconstituted Gal4 activity at the upstream activating sequence (GALUAS) thereby inducing transcription of the reporter gene HIS3.

The initial human BBP1 clone (designated clone 14) was obtained by using a yeast 2-hybrid (Y2H) genetic screen developed to identify proteins which interact with human $BAP_{42}$, a potentially more toxic form of BAP. $BAP_{42}$ was expressed fused to the yeast Gal4 DNA-binding domain and was also expressed as free peptide (FIG. 1). This strain was transformed with a human fetal brain cDNA Y2H library. A single clone, denoted #14, from approximately $10^6$ independent transformants, produced consistent reporter gene activation and contained a substantial open reading frame continuous with that of the GAL4 domain. The cDNA insert comprised 984 base pairs, terminating in a poly-A tract. This sequence encoded 201 amino acids (amino acid 68 to amino acid 269 of SEQ ID NO: 2) with two regions of sufficient length and hydrophobicity to transverse a cellular membrane. There are also potential asparagine-linked glycosylation sites. Clone 14 was designated clone pEK196 and was deposited with American Type Culture Collection (ATCC), 10801 University Boulevard, Manassas, Va. 20110-2209, on Apr. 9, 1997 and assigned Accession Number 98399. All deposits referred to in this application refer to deposits with ATCC and all such deposits will be maintained under the terms of the Budapest Treaty on the International Recognition of the Deposit of Microorganisms for the Purposes of Patent Procedure and under conditions that will make them available to the public as of the issue date of any patent granted from this application.

The library-derived plasmid was isolated from clone 14 and used to reconstruct Y2H assay strains. Examination of these strains demonstrated that the BAP fusion protein specifically interacted with the clone 14 protein, although the response was weak. Since protein domains of strong hydrophobicity, such as transmembrane regions, inhibit Y2H responses, (Ozenberger, unpublished data), clone 14 insert was truncated (BBP1Δtm; see Table 2 below for further description) to remove the region of strongest hydrophobicity and retested for interactions with BAP. A much more robust Y2H response was observed with BBP1Δtm, supporting the notion that the deleted sequences encode a potential transmembrane ("tm") anchor. Clone 14 identifies a novel BAP binding protein in the form of a fusion protein.

The BBP1 cDNA sequences contained in clone 14 were identified as lacking the 5' end of the protein coding region as no potential initiating methionine codon was present. Multiple attempts at conventional 5' RACE (rapid amplification of cDNA ends) utilizing a standard reverse-transcriptase only resulted in the addition of 27 nucleotides. Thus, a genomic cloning approach as described in Example 2, below, was used to isolate the 5' terminus.

Since the 5' coding sequence terminus was derived from a genomic library, there existed the possibility that this region contained introns. This potentiality was investigated by two methods as described in Example 2, below. The resulting data confirmed the upstream sequences (both from genomic and cDNA sources) and the lack of introns in this region. Plasmid BBP1-fl containing a cDNA insert encoding the full length BBP1 protein coding region was deposited in the American Type Culture Collection with accession number 98617 on Dec. 11, 1997. The entire coding region and deduced protein sequence is shown in SEQ ID NOS:1 and 2. The 3' nontranslated nucleotide sequences are contained in the original clone 14 (pEK196).

In accordance with the present invention, nucleotide sequences which encode BBP1, fragments, fusion proteins or functional equivalents thereof, may be used to generate recombinant DNA molecules that direct the expression of BBP1, or a functionally active peptide, in appropriate host cells. Alternatively, nucleotide sequences which hybridize to portions of the BBP1 sequence may be used in nucleic acid hybridization assays, Southern and Northern blot assays, etc.

The invention also includes polynucleotides with sequences complementary to those of the polynucleotides disclosed herein.

The present invention also includes polynucleotides capable of hybridizing under reduced stringency conditions, more preferably stringent conditions, and most preferably highly stringent conditions, to polynucleotides described herein. Examples of stringency conditions are shown in the table below: highly stringent conditions are those that are at least as stringent as, for example, conditions A–F; stringent conditions are at least as stringent as, for example, conditions G–L; and reduced stringency conditions are at least as stringent as, for example, conditions M–R.

TABLE 1

Stringency Conditions

| Stringency Condition | Polynucleotide Hybrid | Hybrid Length (bp)[I] | Hybridization Temperature and Buffer[H] | Wash Temperature and Buffer[H] |
|---|---|---|---|---|
| A | DNA:DNA | >50 | 65° C.; 1xSSC -or- 42° C.; 1xSSC, 50% formamide | 65° C.; 0.3xSSC |
| B | DNA:DNA | <50 | $T_B$*; 1xSSC | $T_B$*; 1xSSC |
| C | DNA:RNA | >50 | 67° C.; 1xSSC -or- 45° C.; 1xSSC, 50% formamide | 67° C.; 0.3xSSC |
| D | DNA:RNA | >50 | $T_D$*; 1xSSC | $T_D$*; 1xSSC |
| E | RNA:RNA | $50 | 70° C.; 1xSSC -or- 50° C.; 1xSSC, 50% formamide | 70° C.; 0.3xSSC |
| F | RNA:RNA | <50 | $T_F$*; 1xSSC | $T_f$*; 1xSSC |
| G | DNA:DNA | >50 | 65° C.; 4xSSC -or- 42° C.; 4xSSC, 50% formamide | 65° C.; 1xSSC |

TABLE 1-continued

Stringency Conditions

| Stringency Condition | Polynucleotide Hybrid | Hybrid Length (bp)[I] | Hybridization Temperature and Buffer[H] | Wash Temperature and Buffer[H] |
|---|---|---|---|---|
| H | DNA:DNA | <50 | $T_H$*; 4xSSC | $T_H$*; 4xSSC |
| I | DNA:RNA | >50 | 67° C.; 4xSSC -or- 45° C.; 4xSSC, 50% formamide | 67° C.; 1xSSC |
| J | DNA:RNA | <50 | $T_J$*; 4xSSC | $T_J$*; 4xSSC |
| K | RNA:RNA | >50 | 70° C.; 4xSSC -or- 50° C.; 4xSSC, 50% formamide | 67° C.; 1xSSC |
| L | RNA:RNA | <50 | $T_L$*; 2xSSC | $T_L$*; 2xSSC |
| M | DNA:DNA | >50 | 50° C.; 4xSSC -or- 40° C.; 6xSSC, 50% formamide | 50° C.; 2xSSC |
| N | DNA:DNA | <50 | $T_N$*; 6xSSC | $T_N$*; 6xSSC |
| O | DNA:RNA | >50 | 55° C.; 4xSSC -or- 42° C.; 6xSSC, 50% formamide | 55° C.; 2xSSC |
| P | DNA:RNA | <50 | $T_P$*; 6xSSC | $T_P$*; 6xSSC |
| Q | RNA:RNA | >50 | 60° C.; 4xSSC -or- 45° C.; 6xSSC, 50% formamide | 60° C.; 2xSSC |
| R | RNA:RNA | <50 | $T_R$*; 4xSSC | $T_R$*; 4xSSC |

[I]: The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
[H]: SSPE (1xSSPE is 0.15M NaCl, 10 mM $NaH_2PO_4$, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete.
*$T_B$–$T_R$: The hybridization temperature for hybrids anticipated to be less than 50 base pairs in length should be 5–10° C. less than the melting temperature ($T_m$) of the hybrid, where $T_m$ is determined according to the following equations.
For hybrids less than 18 base pairs in length, $T_m$(° C.) = 2(# of A + T bases) + 4(# of G + C bases).
For hybrids between 18 and 49 base pairs in length, $T_m$(° C.) = 81.5 + 16.6($\log_{10}$[$Na^+$]) + 0.41(% G + C) − (600/N), where N is the number of bases in the hybrid, and [$Na^+$] is the concentration of sodium ions in the hybridization buffer ([$Na^+$] for 1xSSC = 0.165M).

Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3–6.4, incorporated herein by reference.

Preferably, each such hybridizing polynucleotide has a length that is at least 25% (more preferably at least 50%, and most preferably at least 75%) of the length of the polynucleotide of the present invention to which it hybridizes, and has at least 60% sequence identity (more preferably, at least 75% identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

Expression of BBP1

The isolated polynucleotide of the invention may be operably linked to an expression control sequence such as the pMT2 or pED expression vectors disclosed in Kaufman et al., Nucleic Acids Res. 19, 4485–4490 (1991), in order to produce the protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

Expression Systems for BBP1

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe, Kluyveromyces* strains, *Candida*, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac7 kit), and such methods are well known in the art, as described in Summers and Smith, Texas Agricultural Experiment Station Bulletin No. 1555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl7 or Cibacrom blue 3GA Sepharose7; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and InVitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

Yeast 2 Hybrid Assays

Y2H assays demonstrated that the association of BAP with the BBP1 fusion protein is specific. The association of BBP1 with BAP suggests that BBP1 activity may have a defined role in the pathogenesis of Alzheimer's disease.

BBP1 sequences were compared to Genbank using the basic local alignment search tool (BLAST; Altschul et al., 1990). The BBP1 protein and translations of available expressed sequence tags were aligned, searched for conserved segments, and evaluated by the MoST (Tatusov, et al., 1994) protein motif search algorithm. These analyses revealed a potential evolutionary relationship to the G protein-coupled receptor (GPCR) family. Specifically, these analyses indicated that BBP1 contains two potential transmembrane (tm) domains equivalent to tm domains 3 and 4 of G protein-coupled receptors. The intervening hydrophilic loop contains a well-characterized three amino acid motif, aspartate (D) or glutamate followed by arginine (R) and an aromatic residue (Y or F) (commonly referred to as the DRY sequence), that is conserved in almost all members of this receptor family and has been shown to serve as a molecular trigger for G protein activation (Acharya and Karnik, (1996)).

Data from Y2H assays (see FIGS. 2–4) indicate that BBP1 represents a novel protein potentially containing a functional module shared with members of the G protein-coupled receptor superfamily. Specifically, it appears that BBP1 retains the critical DRF sequence (amino acids 199 to amino acids 201 of SEQ ID NO: 2), between two predicted tm domains, and may have the potential to couple to a G protein regulated signaling pathway.

APP has been shown to functionally associate with Gαo (Nishimoto et al., 1993; Yamatsuji et al., 1996) and BBP1 contains a structural motif known to be a Gα protein activating sequence in the related G protein-coupled receptors. Additionally, a hypothesis based on the predicted position and orientation of BBP1 tm domains suggests that the region of the protein that interacts with BAP would be topographically constrained to the same location as BAP in APP.

Y2H assay strains were engineered to evaluate the association of the BBP1 intracellular region with Gα proteins. The predicted intracellular sequences of BBP1 were expressed as a fusion protein and assayed for interactions with C-terminal regions of three Gα proteins. Protein segments used in these experiments are listed in Table 2, below. The BBP1 intracellular loop interacted with all three Gα proteins (FIG. 3), supporting the premise that BBP1 may function as a modulator of G protein activity. These various Y2H assays suggest the intriguing model of a multiple protein complex minimally composed of the integral membrane proteins BBP1 and APP coupled to a heterotrimeric G protein.

TABLE 2

| Plasmids used in yeast 2-hybrid assays | | |
|---|---|---|
| expression plasmid | protein | segment |
| | BAP | |
| pEK162 | (human) | 1–42 |
| pEK240 | (mouse) | 1–42 |
| | BBP1 | |
| pEK196 | (clone 14) | 68–269 |
| pEK198 | (Δtm) | 68–202 |
| pEK219 | (ΔC) | 68–175 |
| pEK216 | (ΔN) | 123–202 |

TABLE 2-continued

Plasmids used in yeast 2-hybrid assays

| expression plasmid | protein | segment |
|---|---|---|
| pOZ339 | (intracellular) Gα | 185–217 |
| pOZ345 | (Gαs) | 235–394 |
| pOZ346 | (Gαo) | 161–302 |
| pOZ348 | (Gαi2) | 213–355 |

Figure 4:
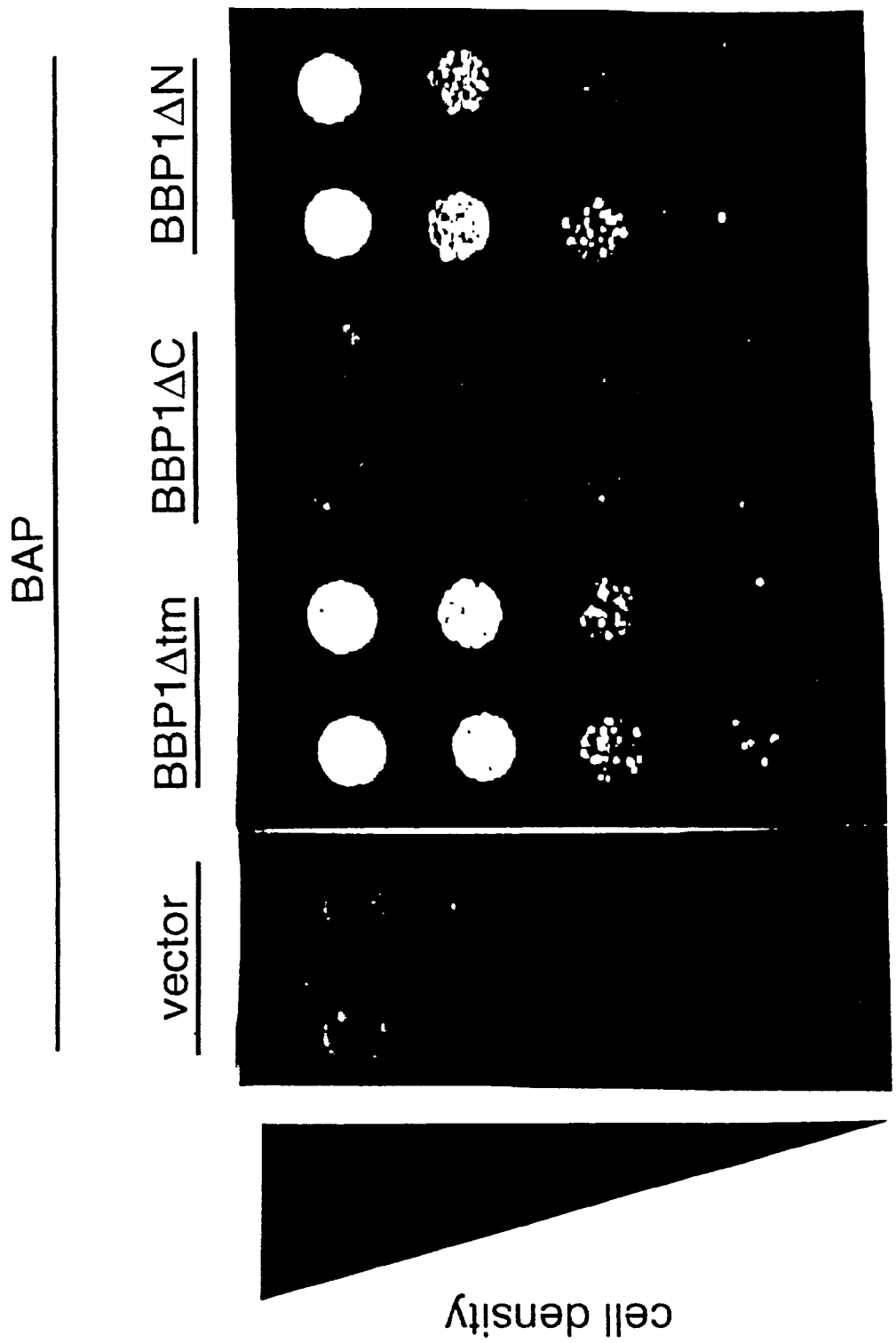
FIG. 4: Localization of the interactions between BBP1 and BAP. BBP1Δtm was divided into two overlapping segments as described in the text. These proteins, BBP1ΔC or BBP1ΔN, were assayed for interactions with BAP. The assay method and the strains labeled vector or BBP1Δtm are as described in the legend to FIG. 2. Strains labeled BBP1ΔC or BBP1ΔN express the indicated BBP1 segment as a fusion protein.

Further analysis of BBP1 was obtained using Y2H assays. Two overlapping portions of the BBP1 sequences contained in the BBP1Δtm clone were amplified and cloned into the Y2H vector pACT2 (expression plasmids pEK216 and pEK219, Table 2 and corresponding proteins BBP1ΔN and BBP1ΔC, (FIG. 4)). The ΔC construct lacked both tm domains; the ΔN construct encoded the first tm domain plus the proceeding 52 amino acids. These fusion proteins were assayed with the BAP fusion protein and responses compared to those of strains expressing the larger BBP1Δtm protein. The BBP1ΔC protein induced a weak Y2H response (compare BBP1ΔC to vector, FIG. 4), but the BBP1ΔN protein, containing the first tm domain and adjacent amino-proximal sequences produced a response only slightly weaker than that observed with BBP1Δtm (FIG. 4). These results suggest that a major determinant for the association with BAP is contained within the BBP1 region predicted to be topographically similar to BAP in the wild-type APP protein.

Figure 7:
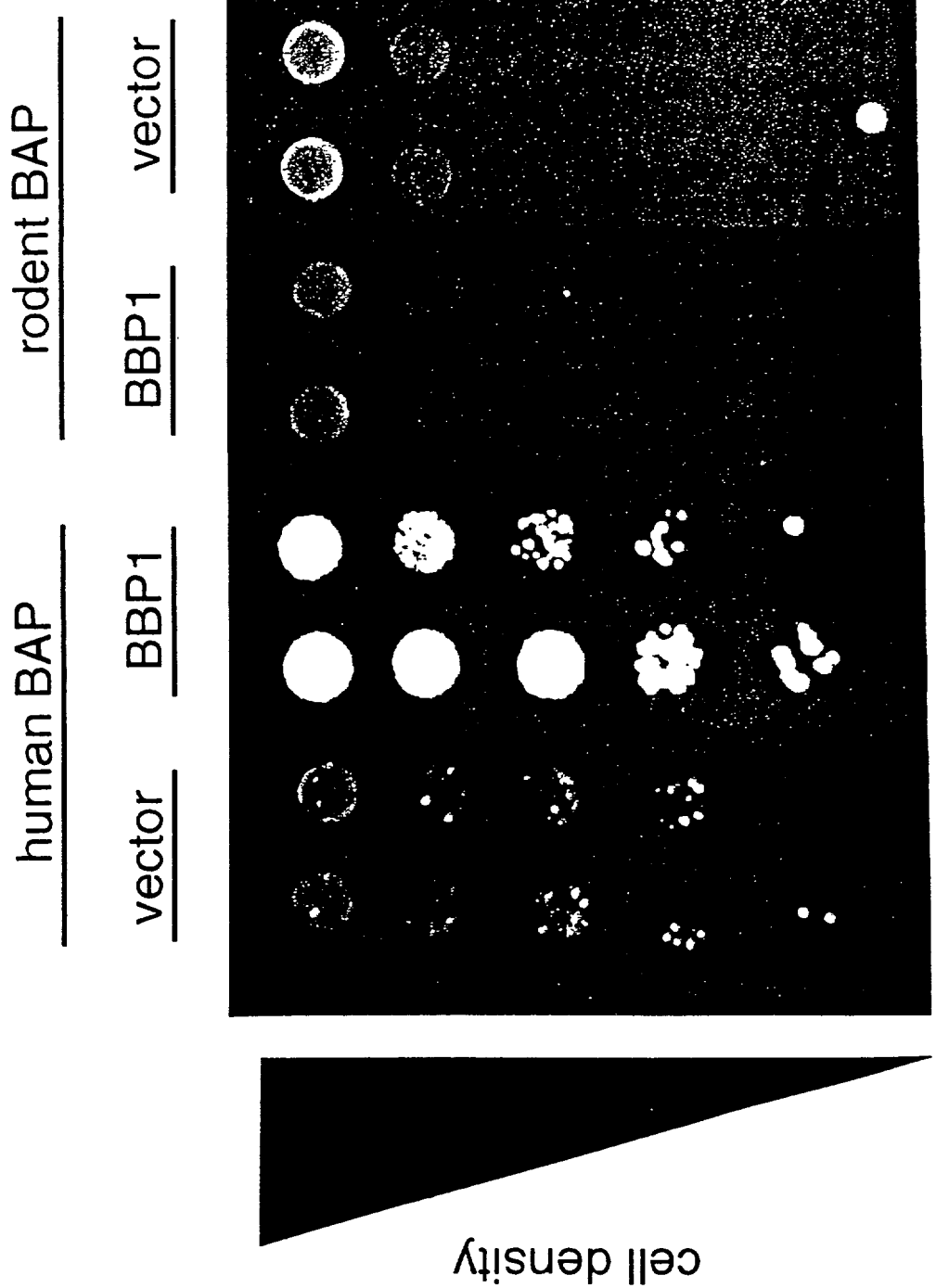
FIG. 7: Comparison of BBP1 interactions with human or rodent BAP. Rodent BAP was engineered and expressed as a fusion protein as described in the text. The strains labeled human BAP are identical to those shown in FIG. 2. The strains labeled rodent BAP express rodent BAP as the Gal4 DNA-binding domain fusion. Vector indicates control strains containing only vector opposing the BAP fusion proteins; BBP1 indicates strains expressing the BBP1Δtm fusion protein.

The Y2H system was utilized to demonstrate the selectivity and specificity of BBP1 binding to human BAP as compared to rodent BAP. There are three amino acid substitutions (G5R, F10Y and R13H) in the rodent BAP sequence compared to the human sequence. It was of interest, to evaluate the association of rodent BAP with BBP1 in the Y2H system. The sequence of human BAP in pEK162 was changed to encode the rodent peptide by oligonucleotide directed mutagenesis by PCR. The resultant plasmid, pEK240, is identical to the human BAP fusion protein expression plasmid utilized throughout this report except for the three codons producing the amino acid substitutions for the rodent peptide sequence. Interactions between BBP1 fusion protein and rodent and human BAP fusion proteins were compared by Y2H bioassay. Strains expressing BBP1 and the rodent BAP failed to produce a growth response (FIG. 7). This finding supports the premise that BBP1 may serve as a specific mediator of the neurotoxic effects of BAP, and provides a mechanism to explain the reduced neurotoxicity of the rodent BAP. Importantly, these data also serve to illustrate the high degree of specificity of the BBP1/BAP interaction in the Y2H assays since the substitution of three amino acids was sufficient to completely abrogate the association (FIG. 7).

Isolated BBP1 Polypeptides

Proteins and protein fragments of the present invention include proteins with amino acid sequence lengths that are at least 25% (more preferably at least 50%, and most preferably at least 75%) of the length of a disclosed protein and have at least 60% sequence identity (more preferably, at least 75% identity; most preferably at least 90% or 95% identity) with that disclosed protein, where sequence identity is determined by comparing the amino acid sequences of the proteins when aligned so as to maximize overlap and identity while minimizing sequence gaps. Also included in the present invention are proteins and protein fragments that contain a segment preferably comprising 8 or more (more preferably 20 or more, most preferably 30 or more) contiguous amino acids that shares at least 75% sequence identity (more preferably, at least 85% identity; most preferably at least 95% identity) with any such segment of any of the disclosed proteins.

Species homologues of the disclosed polynucleotides and proteins are also provided by the present invention. As used herein, a species homologue is a protein or polynucleotide with a different species of origin from that of a given protein or polynucleotide, but with significant sequence similarity to the given protein or polynucleotide. Preferably, polynucleotide species homologues have at least 60% sequence identity (more preferably, at least 75% identity; most preferably at least 90% identity) with the given polynucleotide, and protein species homologues have at least 30% sequence identity (more preferably, at least 45% identity; most preferably at least 60% identity) with the given protein, where sequence identity is determined by comparing the nucleotide sequences of the polynucleotides or the amino acid sequences of the proteins when aligned so as to maximize overlap and identity while minimizing sequence gaps. Species homologues may be isolated and identified by making suitable probes or primers from the sequences provided herein and screening a suitable nucleic acid source from the desired species. Preferably, species homologues are those isolated from certain mammalian species. Most preferably, species homologues are those isolated from certain mammalian species such as, for example, *Pan troglodytes, Gorilla gorilla, Pongo pygmaeus, Hylobates concolor, Macaca nulatta, Papio papio, Papio hamadryas, Cercopithecus aethiops, Cebus capucinus, Aotus trivirgatus, Sanguinus oedipus, Microcebus murinus, Mus musculus, Rattus norvegicus, Cricetulus griseus, Felis catus, Mustela vison, Canis familiaris, Oryctolagus cuniculus, Bos taurus, Ovis aries, Sus scrofa,* and *Equus caballus*, for which genetic maps have been created allowing the identification of syntenic relationships between the genomic organization of genes in one species and the genomic organization of the related genes in another species (O'Brien and Seuanez, 1988, Ann. Rev. Genet. 22: 323–351; O'Brien et al., 1993, Nature Genetics 3:103–112; Johansson et al., 1995, Genomics 25: 682–690; Lyons et al., 1997, Nature Genetics 15: 47–56; O'Brien et al., 1997, Trends in Genetics 13(10): 393–399; Carver and Stubbs, 1997, Genome Research 7:1123–1137; all of which are incorporated by reference herein).

The invention also encompasses allelic variants of the disclosed polynucleotides or proteins; that is, naturally-occurring alternative forms of the isolated polynucleotides which also encode proteins which are identical or have significantly similar sequences to those encoded by the disclosed polynucleotides. Preferably, allelic variants have at least 60% sequence identity (more preferably, at least 75% identity; most preferably at least 90% identity) with the given polynucleotide, where sequence identity is determined by comparing the nucleotide sequences of the polynucleotides when aligned so as to maximize overlap and identity while minimizing sequence gaps. Allelic variants may be isolated and identified by making suitable probes or primers from the sequences provided herein and screening a suitable nucleic acid source from individuals of the appropriate species.

The invention also includes polynucleotides with sequences complementary to those of the polynucleotides disclosed herein.

Applications

BBP1 proteins of the present invention can be used in a variety of applications routine to one of skill in the art based upon this disclosure. Specifically the BBPs can be used as immunogens to raise antibodies which are specific to the cloned polypeptides. Various procedures known in the art may be used for the production of antibodies to BBP1 proteins. Such antibodies include, but are not limited to, polyclonal, monoclonal, chimeric, single chain, Fab fragments and a Fab expression library. For the production of antibodies, various host animals including, but not limited to rabbits, mice, and rats, are injected with a BBP. In one embodiment, the polypeptide or a fragment of the polypeptide capable of specific immunoactivity is conjugated to an immunogenic carrier. Adjuvants may also be administered in conjunction with the polypeptide to increase the immunologic response of the host animal. Examples of adjuvants which may be used include, but are not limited to, complete and incomplete Freund's, mineral gels such as aluminum hydroxide, surface active substances such as lysolecithin, pluronic polyols, polyanions, peptides, oil emulsions, keyhole limpet hemocyanin, and dinitrophenol.

Monoclonal antibodies to BBP1 proteins of the present invention can be prepared using any technique which provides for the production of antibodies by continuous cell line in culture. Such techniques are well known to those of skill in the art and include, but are not limited to, the hybridoma technology originally described by Kohler and Milstein (Nature 1975, 256,4202–497), the human B-cell hybridoma technique described by Kosbor et al. (Immunology Today 1983, 4, 72) and the EBV-hybridoma technique described by Cole et al. (Monoclonal Antibodies and Cancer Therapy, Alan R. Liss, Inc., pp 77–96).

Antibodies immunoreactive to the polypeptides of the present invention can then be used to screen for the presence and subcellular distribution of similar polypeptides in biological samples. In addition, monoclonal antibodies specific to the BBP1 proteins of the present invention can be used as therapeutics.

The BBP1 proteins can also serve as antigens useful in solid phase assays measuring the presence of antibodies which immunoreact with the claimed peptides. Solid phase competition assays can be used to measure immunological quantities of clone 14-related antigen in biological samples. This determination is not only useful in facilitating the complete characterization of the cellular function or functions of the polypeptides of the present inventions, but can also be used to identify patients with abnormal amounts of these proteins.

BBP1 proteins of the present invention can also be used as capture reagents in affinity chromatography for the detection of BAP and BAP aggregates as markers for AD.

In addition, these BBP1s are useful as reagents in an assay to identify candidate molecules which effect the interaction of BAP and the cloned protein. Compounds that specifically block this association could be useful in the treatment or prevention of AD.

These BBP1s are also useful in acellular in vitro binding assays wherein alteration by a compound in the binding of these beta amyloid peptide associated proteins to BAP or BAP aggregates is determined. Acellular assays are extremely useful in screening sizable numbers of compounds since these assays are cost effective and easier to perform than assays employing living cells. Upon disclosure of the polypeptides of the present invention, the development of these assays would be routine to the skilled artisan.

In such assays, either BBP1 or BAP is labeled. Such labels include, but are not limited to, radiolabels, antibodies, and fluorescent or ultraviolet tags. Binding of a BBP1 to BAP or BAP aggregates is first determined in the absence of any test compound. Compounds to be tested are then added to the assay to determine whether such compounds alter this interaction.

EXAMPLES

The present invention is further described by the following examples. The examples are provided solely to illustrate the invention by reference to specific embodiments. These exemplifications, while illustrating certain specific aspects of the invention do not portray the limitations or circumscribe the scope of the invention.

Yeast two-hybrid system (hereinafter "Y2H"): Y2H expression plasmids were constructed in vectors pAS2 and pACT2 (described in Wade Harper et al., 1993) and pCUP (described in Ozenberger and Young, 1995). Yeast strain CY770 (Ozenberger and Young, 1995) served as the host for all Y2H assays.

Genetic screen: The polymerase chain reaction (PCR) method was used to amplify and modify sequences encoding BAP. Oligonucleotides #1 (5'-CC ATG GAT GCA GAA TTC CGA C (SEQ ID NO:3)) and #3 (5'-AAGCTTGTC-GAC TTA CGC TATGAC AAC ACC GC (SEQ ID NO:4)) were used to amplify BAP using pCLL621, a modified human APP clone (Jacobsen et al., 1994), as template. The amplified DNA consists of codons 389 to 430 (which encodes $BAP_{42}$) of the APP precursor protein with the following modifications. The sense strand primer added a 5' NcoI restriction site in the same translational reading frame as the NcoI site in pAS2. The antisense strand primer added a stop codon and HindIII and SalI sites for cloning. The product from this amplification was ligated into the TA cloning system (Invitrogen Corp., Carlsbad, Calif.), and subsequently removed by digestion with NcoI and SalI. This fragment was cloned into pAS2 cleaved with NcoI plus SalI. The resultant plasmid, pEK162, was confirmed by DNA sequencing through the GAL4/BAP junction. The protein ($BAP^{BD}$; FIG. 1) expressed from pEK162 comprised a fusion protein containing the DNA-binding domain of the yeast transcriptional activation protein Gal4 (lacking functional activation sequences) with the addition of the 42 amino acids of BAP to the carboxy-terminus. An expression plasmid was developed that mediates the expression of unmodified $BAP_{42}$. Oligo #2 (5'-AAGCTTAAG ATG GAT GCA GAA TTC CGA C (SEQ ID NO:5)) was paired with oligo #3 in a PCR as described above. The product of this amplification contains a 5' HindIII site and translation initiation signals optimized for expression in *Saccharomyces cerevisiae*. Again, the DNA fragment was cloned into the TA system. It was then isolated on a HindIII fragment and cloned into pCUP cleaved with HindIII. The orientation of the BAP gene in the resultant plasmid, pEK149 (BAP; FIG. 1), was confirmed by DNA sequencing. The BAP expression plasmids pEK149 (which used URA3 as the selection marker) and pEK162 (which used TRP1 as the selection marker) were transformed into the yeast host CY770 (Ozenberger and Young, 1995). The strain containing both plasmids was designated CY2091. A plasmid library consisting of cDNA fragments isolated from human fetal brain cloned into the yeast 2-hybrid expression vector pACT2 (which used LEU2 as the selection marker) was purchased from Clontech Laboratories, Inc. (Palo Alto, Calif.). The library-derived protein is depicted in FIG. 1 as unknown$^{AD}$. This library was used to transform CY2091. The samples were spread on synthetic complete (SC) yeast growth medium lacking uracil, tryptophan, and leucine to select cells containing all three plasmids. The medium also lacked histidine and contained 3-amino-triazole, an inhibitor of the product of the yeast HIS3 gene, at a concentration of 25 mM. 3-Amino-triazole was utilized to reduce activity from low-level constitutive expression of the HIS3 reporter gene. Plates were incubated at 30° C. for 12 days. Twenty-four colonies exhibiting increased histidine prototrophy were isolated. Transformation controls indicated that the screen assayed $10^6$ individual clones. A PCR approach was utilized to quickly determine the content of positive clones. Total DNA was isolated from each positive strain by standard methods. This material was used as template for PCRs using oligos #4 (5'-TTTAATACCA CTACAATGGA T (SEQ ID NO:6)) plus #5 (5'-TTTTCAGTAT CTACGATTCA T (SEQ ID NO:7)) which flank the cloning region of the library vector pACT2. DNA fragments were ligated into the TA system and examined by DNA sequencing. The library plasmid contained in clone #14 (as described above) was isolated by shuttle into E. coli. The nucleotide sequence of the human cDNA sequences was determined, confirming the sequence of the initial PCR product.

Bioassays: Strains were grown overnight in 2 ml SC medium lacking leucine and tryptophan to a density of approximately $7\times10^7$ cells per ml. Cells were counted and 10-fold serial dilutions made from $10^4$ to $10^8$ cells per ml in sterile water. These samples were spotted in 5 µl aliquots on SC medium lacking leucine, tryptophan and histidine and containing 25 mM 3-amino-triazole. Plates were incubated at 30° C. for 2 to 3 days. Positive protein/protein interactions were identified by increased prototrophic growth compared to control strains expressing the Gal4 DNA-binding domain fusion protein plus an irrelevant transcriptional activation domain fusion protein (or simply containing the pACT vector without inserted sequences). These control strains were indicated in the Figures described above as the label 'vector'. This assay method was highly reproducible and provided for the detection of subtle inductions of growth mediated by the specific interaction between target proteins. The original BBP1 clone, designated pEK196 and deposited as ATCC 98399; is referred herein as clone 14), was used as a PCR template to truncate the protein product to express BBP1Δtm. Sense primer #6 (5'-TTTAATACCA CTA-CAATGGA T (SEQ ID NO:8)) annealed to GAL4 sequences in pACT2. The antisense primer #7 (5'-CTCGAG TTA AAA TCG ATC TGC TCC CAA CC (SEQ ID NO:9)) incorporated a 3' stop codon and XhoI site immediately 3' to the sequences encoding the DRF motif of BBP1. The PCR product was ligated into the TA cloning vector and subsequently digested with EcoRI+XhoI and cloned into pACT2. The hybrid product expressed from this plasmid (pEK198) was denoted BBP1Δtm. Similarly, primer #7 was paired with primer #8 (5'-GAATT CCA AAA ATA AAT GAC GCT ACG (SEQ ID NO:10)) to engineer the BBP1ΔN expression plasmid pEK216. Again, the PCR product was ligated into the TA system and the resultant plasmid digested with EcoRI+XhoI with the BBP1 fragment (codons 123–202) finally ligated into pACT2 digested with the same enzymes. BBP1ΔC was made by using the pACT2-specific oligo #6 with antisense oligo #9 (5'-CTCGAG TCA AGA TAT GGG CTT GAA AAA AC (SEQ ID NO:11)). After TA cloning, isolation of the EcoRI–XhoI fragment and cloning into pACT2, the resultant plasmid, pEK219, expressed BBP1 from residue 68 to 175. Sequences encoding the BBP1 intracellular loop were amplified using oligonucleotides #10 (5'-CCTTCC ATG GAA GTG GCA GTC GCA TTG TCT (SEQ ID NO:12)) plus #11 (5'-AACACTCGAG TCA AAA CCC TAC AGT GCA AAA C (SEQ ID NO:13)). This product, containing BBP1 codons 185 to 217, was digested with NcoI+XhoI and cloned into pAS2 cleaved with NcoI+SalI to generate pOZ339. Construction of all Gα protein expression plasmids utilized the BamHI site near the center of each rat cDNA sequence (Kang et al., 1990) as the site of fusion in pACT2. Sense primers annealed to sequences 5' of the BamHI site; antisense primers annealed to sequences 3' of the stop codon and included a SalI restriction site. Primers were: Gαo, sense (#17)=5'-GTG-GATCCAC TGCTTCGAGG AT (SEQ ID NO:14), antisense (#18)=5'-GTCGACGGTT GCTATACAGG ACAA-GAGG (SEQ ID NO:15); Gαs, sense (#19)=5'-GTGGATCCAG TGCTTCAATG AT (SEQ ID NO:16), antisense (#20)=5'-GTCGACTAAA TTTGGGCGTT CCCTTCTT (SEQ ID NO:17); Gαi2, sense (#21)=5'-GTG-GATCCAC TGCTTTGAGG GT (SEQ ID NO:18), antisense (#22)=5'-GTCGACGGTC TTCTTGCCCC CATCT-TCC (SEQ ID NO:19). PCR products were cloned into the TA vector. Gα sequences were isolated as BamHI-SalI fragments and cloned into pACT2 digested with BamHI+SalI. See Table 2 for plasmid designations. Finally, oligonucleotide #23 was synthesized for the conversion of human BAP to the rodent sequence. This primer has the sequence 5'-ATATGGCCATG GAT GCA GAA TTC GGA CAT GAC TCA GGA TTT GAA GTT CGT (SEQ ID NO:20). The triplets represent the first 13 codons of BAP; the three nucleotides that were changed to produce the rodent sequence are underlined. Oligo #23 was paired with #24 (5'-TGACCTACAG GAAAGAGTTA (SEQ ID NO:21)) which anneals to a region of the Y2H vectors that is 3' of the cloning site in a PCR using pEK162 as the template. The product was cleaved with NcoI+SalI and ligated into pAS2 to produce pEK240. The nucleotide sequence of the segment encoding rodent BAP was confirmed.

Figure 2:
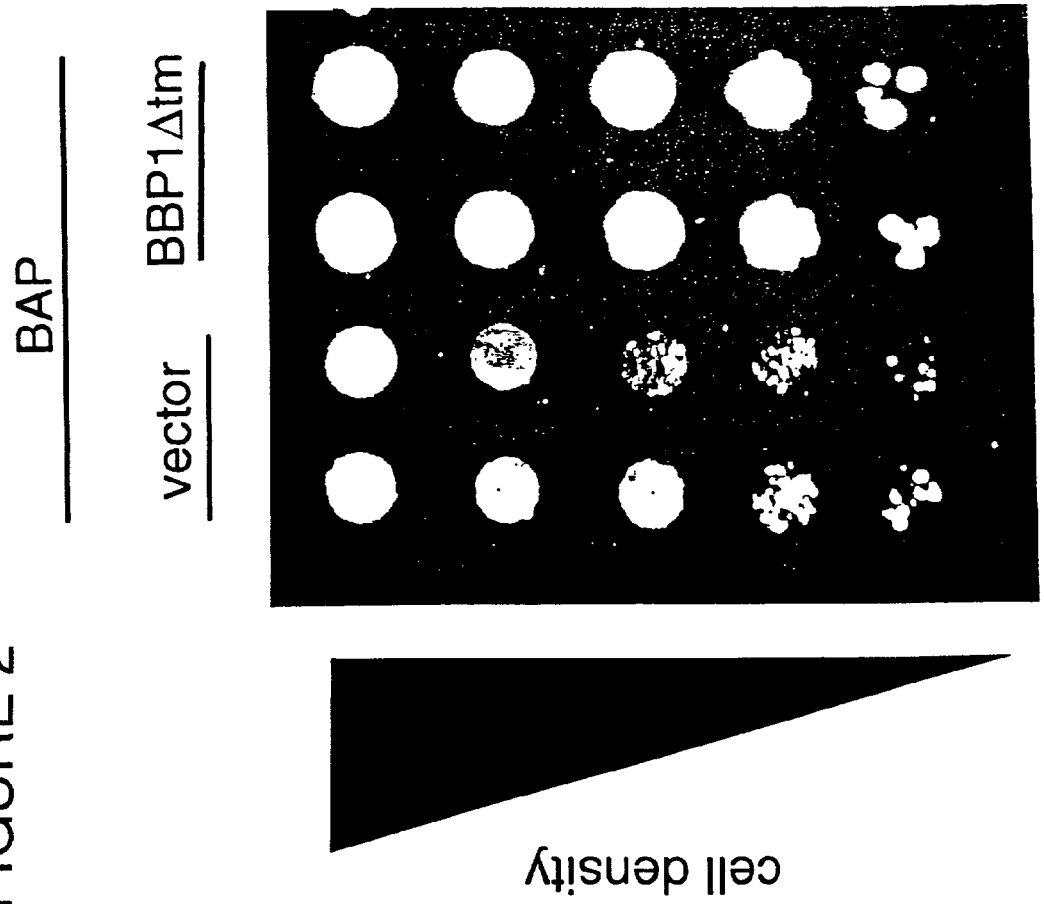
FIG. 2: Demonstration of BBP1/BAP association. Y2H strains were assayed for histidine prototrophy by making 10-fold serial dilutions and spotting 5 μl on synthetic agar medium lacking tryptophan, leucine, histidine and containing 25 mM 3-amino-triazole as described. All strains contain the BAP fusion protein expression plasmid pEK162 as indicated by the label BAP. The first columns (vector) contain independently derived strains carrying pEK162 and the vector pACT2 expressing an irrelevant fusion protein. These serve as a measure of background for comparison with strains expressing target proteins. The columns marked by BBP1Dtm express a truncated BBP1 from pEK198, as described in the text. The interaction between BAP and BBP1Δtm fusion proteins reconstitutes Gal4 activity, resulting in induction of a HIS3 reporter gene (see FIG. 1), observed as enhanced prototrophic growth compared to the control strains.

Genomic cloning: RACE (rapid amplification of cDNA ends): A human genomic lambda library (Stratagene), corresponding to $2.0\times10^6$ pfus, was screened with randomly-primed EcoRI/C1aI fragment probe corresponding to nucleotides 187–600 (FIG. 2). The probe was labeled with [$^{32}$P]-CTP using the $^{T7}$QuickPrimer Kit according to the manufacturer's (Pharmacia) protocol. Filters were hybridized under high stringency: 40° C. in 50% formamide, 0.12 M NaHPO$_4$, 0.25 M NaCl, 7% SDS and 25 mg/ml sonicated salmon sperm DNA and washed at 65° C. in 0.1×SSC containing 0.1% sodium dodecyl sulfate and exposed to, Kodak BioMax MS film. Lambda phage clones hybridizing to the probe were plaque purified by successive plating and rescreening. Ten positive clones were purified and subjected to further analysis by hybridization to a 45 nt oligonucleotide probe directed to the most 5' sequences known from the original cDNA clone. This oligonucleotide was the reverse complement of nucleotides. 157–201 (SEQ ID NO:2) and has the sequence 5'-CCAGGCGGCC GCCATCTTGG AGACCGACAC TTTCTCGCCA CTTCC (SEQ ID NO:22). Lambda phage DNA was isolated by standard molecular biology techniques and subjected to direct sequencing using fluorescent dideoxy cycle sequencing on an ABI 373 sequencer.

RACE: First strand DNA synthesis was performed using the rTth thermal-stable polymerase system (Perkin Elmer). The following reagents were combined in a 1.5 mL tube to give a 10 microliter volume: 1× reverse transcription buffer, 1 mM MnCl$_2$, 1.6 mM dNTP mix, 2.5 U rTth polymerase, 100 ng human hippocampus poly A+ RNA (Clontech), 10 mM oligonucleotide (nt 429–452, SEQ ID NO:2; 5'-GTTAT-GTTGG GTGCTGGAAA ACAG (SEQ ID NO:23)). The reaction was incubated at 70° C. for 15 minutes and immediately placed on ice. The Marathon cDNA synthesis kit (Clontech) was used for second strand cDNA generation. The entire 10 µl from the first strand reaction was combined with the following reagents: 1× second strand buffer, 0.8 mM dNTP mix, 4× second strand cocktail (*E. coli* DNA polymerase I, *E. coli* DNA ligase, *E. coli* RNaseH), and dH$_2$O up to a volume of 80 µl. The tube was incubated at 16° C. for 1.5 hours after which time T4 DNA polymerase (10 U) was added and incubated for an additional 45 minutes at 16° C. To terminate the reaction, 4 µl of 20×EDTA/glycogen (0.2M EDTA/2 mg/ml glycogen) was added to the reaction mixes followed by a phenol/chloroform/isoamyl alcohol extraction to remove enzymes and other impurities. The DNA was precipitated by adding 0.1× volume 3M Na acetate pH 5.2 and 2.5× volume reagent grade EtOH and place at −70° C. The DNA was washed once with 70% EtOH, dried down and resuspended in 10 µl dH$_2$O. Half of the DNA was used for Marathon adaptor ligation to be used in subsequent RACE PCR reactions following the Clontech protocol as follows: 5 µl cDNA was added to 2 µl (10 mM) Marathon (5'-CTAATACGAC TCACTATAGG GCTC-GAGCGG CCGCCCGGGC AGGT (SEQ ID NO:24)), 1×DNA ligation buffer and 1 µl (1 U) T4 DNA ligase. The reaction mix was incubated overnight at 16-C. The mix was diluted 1:50 for initial RACE reaction and combined in a 0.2 mL PCR tube with the following: 40 µl dH$_2$O, 1 µl 10× Klentaq DNA polymerase (Clontech), 1 µl (10 mM) AP1 primer (5'-CCATCCTAAT ACGACTCACT ATAGGGC (SEQ ID NO:25)), 1 µl (10 mM) BBP1-specific primer (corresponding to nts. 187–209, SEQ ID NO:2; 5'-CCA-GACGGCCA GGCGGCCGCC AT (SEQ ID NO:26)), 5 µl 10× Klentaq polymerase buffer, 1 µl 10 mM dNTP mix, 1 µl of diluted cDNA from above reaction. The following cycling conditions were performed using a Perking Elmer GeneAmp PCR system 2400 thermocycler: Denaturing cycle 94-C for 1 minute followed by 5 cycles of 30" at 94° C., 3' at 72° C., 5 cycles of 30" at 94° C., 3' at 70° C., followed by 25 cycles of 30" at 94° C., 3' at 68° C., with a final extension 7' at 72° C. This was followed by a nested RACE PCR reaction as follows: 40 µl dH$_2$O, 191 (1 U) 10× AmplitaqGold DNA polymerase (Perkin Elmer), 1 µl (10 mM) AP2 primer (5'-ACTCACTATA GGGCTCGAGC GGC (SEQ ID NO:27)), 1 µl (10 mM) BBP1-specific primer (corresponding to nts. 172–194, SEQ ID NO:2; 5'-GCCGCCATCT TGGAGACCGA CAC (SEQ ID NO:28)), 5 µl 10× Amplitaq polymerase buffer, 1 µl 10 mM dNTP mix, 1 µl of primary RACE product. The PCR cycling conditions were an initial denaturing cycle of 9' at 94° C., 25 cycles of 30" at 94° C., 30" at 68° C., 2' at 72° C., followed by a 72° C. extension for 7'. The PCR product was run on a 1% agarose gel in 1×TBE buffer. The resulting 350 base pairs product was gel purified and directly cloned using the TA Cloning Kit (Invitrogen). Ligation mixes were transformed into OneShot Cells (Invitrogen) and plated on LB-ampicillin (100 µg/ml) agar plates containing X-gal. Mini-prep DNA was obtained and examined by fluorescent dideoxy cycle sequencing on an ABI 373 sequencer.

Northern analyses: Human multiple tissue and multiple brain tissue mRNA Northern blots were obtained from Clontech (Palo Alto, Calif.). BBP1 sequences extending from the original fusion junction to the poly-A region were isolated on an EcoRI fragment from a TA clone derived from pEK196. β-actin DNA was provided by the manufacturer. Radiolabelled probes were produced from these DNAs using a random priming method to incorporate $^{32}$P-dCTP (Pharmacia Biotech, Piscataway, N.J.). Hybridizations were performed per manufacturer's (Clontech) instructions in Express Hyb Solution at 68° C. Blots were washed in 2×SSC (1×SSC is 0.15 M sodium chloride, 0.015 M sodium citrate), 0.05% SDS at room temperature, followed by two washes in 0.1×SSC, 0.1% SDS at 50° C. Hybridization signals were visualized by exposure to Kodak BioMax film.

In situ hybridization: DNA templates for riboprobe synthesis were prepared by PCR using a plasmid clone containing the full length human BBP cDNA. A single riboprobe targeted to the 3' UTR of the cDNA was used. The probe sequences were checked versus the GenBank database to ensure that they only recognize the appropriate targets among all deposited sequences. To generate riboprobes for BBP1, a pair of oligonucleotide primers was designed to amplify a 275 base pairs region from the 3' UTR of the BBP1 cDNA and, in addition, add the promoter sequences for T7 (sense) and T3 (antisense) polymerase. These primers contained the following sequences: 5'-TAATACGACT CACTATAGGG TTAGAAGAAA CAGATTTGAG (forward) (SEQ ID NO:29); 5'-ATTAACCCTC ACT-AAAGGGA CAAGTGGCAA CTTGCCTTTG (reverse) (SEQ ID NO:30). PCR products were gel purified on 1.5% low-melt agarose gels, and bands containing the products were excised, phenol and phenol-chloroform extracted, and ethanol precipitated. Pellet were dried and resuspended in 1×TE buffer (10 mM Tris-HCl, 1 mM EDTA, pH 7.4). The APP riboprobe template consisted of a DdeI-XhoI fragment from the protein coding region, as described by Jacobsen et al (1991). Fifty ng of DNA template was used for transcription reactions using ($^{35}$S)-CTP (New England Nuclear, Boston, Mass.) and the Riboprobe Gemini™ System (Promega, Madison, Wis.).

In situ hybridization histochemistry using sections of postmortem human hippocampus were performed as described previously (Rhodes, 1996). Sections were cut at 10 µm on a Hacker-Brights cryostat and thaw-mounted onto chilled (−20° C.) slides coated with Vectabond reagent (Vector Labs, Burlingame, Calif.). All solutions were prepared in dH$_2$O treated with 0.1% (v/v) diethylpyrocarbonate and autoclaved. Sections were fixed by immersion in 4% paraformaldehyde in PBS (pH 7.4) then immersed sequentially in 2×SSC, dH$_2$O, and 0.1 M triethanolamine, pH 8.0. The sections were then acetylated by immersion in 0.1 M triethanolamine containing 0.25% (v/v) acetic anhydride, washed in 0.2×SSC, dehydrated in 50, 70 and 90% ethanol, and rapidly dried. One ml of prehybridization solution containing 0.9 M NaCl, 1 mM EDTA, 5×Denhardt's, 0.25 mg/ml single-stranded herring sperm DNA (GIBCO/BRL, Gaithersberg, Md.), 50% deionized formamide (EM Sciences, Gibbstown, N.J.) in 10 mM Tris, (pH 7.6), was pipetted onto each slide, and the slides incubated for 3 hrs. at 50° C. in a humidified box. The sections were then dehydrated by immersion in 50, 70, and 90% ethanol and air dried. Labeled riboprobes were added at a final concentration of 50,000 cpm/µl to hybridization solution containing 0.9 M NaCl, 1 mM EDTA, 1×Denhardt's, 0.1 mg/ml yeast tRNA, 0.1 mg/ml single-stranded salmon sperm DNA, dextran sulfate (10%), 0.08% BSA, 10 mM DTT (Boehringer Mannheim, Indianapolis, Ind.), and 50% deionized formamide in 10 mM Tris (pH 7.6). The probes were then denatured at 95° C. (1 min), placed on ice (5 min), and pipetted onto the sections and allowed to hybridize overnight at 55° C. in a humidified chamber. The sections were subsequently washed 1×45 min at 37° C. in 2×SSC containing 10 mM DTT, followed by 1×30 min at 37° C. in 1×SSC containing 50% formamide, and 1×30 min at 37° C. in 2×SSC. Single stranded and non-specifically hybridized riboprobe was digested by immersion in 10 mM Tris pH 8.0 containing bovine pancreas RNAse A (Boehringer Mannheim; 40 mg/ml), 0.5 M NaCl, and 1 mM EDTA. The sections were washed in 2×SSC for 1 hr at 60° C., followed by 0.1×SSC containing 0.5% (w/v) sodium thiosulfate for 2 hrs. at 60° C. The sections were then dehydrated in 50, 70, 90% ethanol containing 0.3 M ammonium acetate, and dried. The slides were loaded into X-ray cassettes and opposed to Hyperfilm b-Max (Amersham) for 14–30 days. Once a satisfactory exposure was obtained, the slides were coated with nuclear-track emulsion (NTB-2; Kodak) and exposed for 7–21 days at 4° C. The emulsion autoradiograms were developed and fixed according to the manufacturer's instructions, and the underlying tissue sections were stained with hematoxylin. To assess nonspecific labeling, a control probe was generated from a template provided in the Riboprobe Gemini™ System kit (Promega). This vector was linearized using ScaI and transcribed using T3 polymerase. The resulting transcription reaction generates two products, a 250 base and a 1,525 base riboprobe, containing only vector sequence. This control probe mixture was labeled as described above and added to the hybridization solution at a final concentration of 50,000 cpm/µl. No specific hybridization was observed in control sections, i.e., these sections gave a very weak uniform hybridization signal that did not follow neuroanatomical landmarks (data not shown).

Example 1

Cloning and Isolation BAP-Binding Protein (BBP1)

A yeast 2-hybrid (Y2H) genetic screen was developed to identify proteins which interact with human $BAP_{42}$, a 42 amino acid proteolytic fragment of APP which is considered to potentially be the more toxic aggregated form of BAP. $BAP_{42}$ was expressed fused to the yeast Gal4 DNA-binding domain and was also expressed as free peptide (FIG. 1). This strain was transformed with a human fetal brain cDNA Y2H library. A single clone, designated clone14 defined above, from approximately $10^6$ independent transformants, produced consistent reporter gene activation and contained a substantial open reading frame continuous with that of the GAL4 domain. The cDNA insert comprised 984 base pairs, terminating in a poly-A tract. This sequence encoded 201 amino acids (SEQ ID NO: 2; amino acid residues 68 to 269) with two regions of sufficient length and hydrophobicity to transverse a cellular membrane.

The library-derived plasmid was isolated from clone 14 and used to reconstruct Y2H assay strains. Examination of these strains demonstrated that the BAP fusion protein specifically interacted with the clone 14 protein, although the response was weak. Since protein domains of strong hydrophobicity, such as transmembrane regions, inhibit Y2H responses (Ozenberger, unpublished data), clone 14 insert was truncated (hereinafter BBP1Δtm) to remove the region of strongest hydrophobicity and retested for interactions with BAP. A much more robust Y2H response was observed with BBP1Δtm (FIG. 2), supporting the notion that the deleted sequences encode a potential transmembrane ("tm") anchor. The nucleotide sequence of Clone 14 was searched against GenBank; the BAP binding protein (BBP1) thus identified appeared to be novel.

Example 2

Isolation and Confirmation of the 5' Terminus of BBP1

The BBP1 cDNA sequences contained in clone 14 described in Example 1, above, lacked the 5' end of the protein coding region as no potential initiating methionine codon was present. Multiple attempts at conventional 5' RACE (rapid amplification of cDNA ends) utilizing a standard reverse-transcriptase only resulted in the addition of 27 nucleotides. These sequences included an ATG, but no upstream stop codon in the same translational reading frame to provide confidence that this was the initiating codon. A genomic cloning approach was initiated to isolate the 5' terminus of the BBP1 gene.

Hybridization of a human genomic lambda library with a randomly-primed probe corresponding to 400 base pairs (bps) of the 5' sequence of clone 14 resulted in identification of 10 positive clones. Further characterization of these clones using a 45-base oligonucleotide probe directed to the most upstream BBP1 sequence of clone 14 (and corresponding to the 5' upstream sequence of the 400 base pairs probe revealed that 6 of the 10 clones included the terminal 5' sequences contained within those previously identified. It was determined that the other 4 lambda clones represented other exons which were contained within the original 400 base pairs randomly-primed cDNA-derived probe (data not shown). Direct cycle sequencing of lambda phage DNA from representative clones corresponding to the 5' end of BBP1 revealed 500 nucleotides upstream and overlapping with the sequence known for clone 14. This additional sequence potentially encodes 62 additional amino acids upstream of the previously characterized MET before arriving at a MET preceded by an in-frame stop codon. Although there exist two MET residues downstream from the furthest upstream MET, by standard convention we have tentatively defined the sequence of the amino terminus of the human BBP1 gene to include the first 5' MET which follows an in-frame stop codon. The entire coding region and deduced protein sequence is shown in SEQ ID NOS: 1 and 2. A plasmid (denoted BBP1-fl) containing this amino acid sequence has been deposited in the American Type Culture Collection having accession number 98617).

Since the 5' coding sequences were derived from a genomic library, there existed the possibility that this region contained introns. This potentiality was investigated by two methods. First, a forward primer directed to the region of the 5' MET and a reverse primer within the original clone 14 were utilized to amplify sequences from brain cDNA as well as from genomic DNA. Products of identical size were generated from both samples, indicating the absence of introns within this region and confirming the linkage of the upstream sequence with the original sequence. Secondly, cDNA sequences were isolated in modified 5' RACE experiments (see Materials and Methods, above) that were identical to those obtained from the genomic clone. These findings confirmed the upstream sequences (both from genomic and cDNA sources) and the lack of introns in this region.

Example 3

Characterization of BBP1

BBP1 sequences were compared to Genbank using the basic local alignment search tool (BLAST; Altschul et al., 1990). Two *Caenorhabditis elegans* and one *Drosophila melanogaster* genomic sequence and a large number of human, mouse and other mammalian expressed sequence tags were identified. However, no complete cDNA sequences were available nor were any functional data attributed to the gene. The BBP1 protein and translations of available expressed sequence tags were aligned, searched for conserved segments, and evaluated by the MoST (Tatusov et al., 1994) protein motif search algorithm. These analyses revealed a potential evolutionary relationship to the G protein-coupled receptor family. Specifically, these analyses indicated that BBP1 contains two potential transmembrane (tm) domains equivalent to tm domains 3 and 4 of G protein-coupled receptors. The intervening hydrophilic loop contains a well-characterized three amino acid motif, aspartate (D) or glutamate followed by arginine (R) and an aromatic residue (Y or F) (commonly referred to as the DRY sequence), that is conserved in almost all members of this receptor family and has been shown to serve as a molecular trigger for G protein activation (Acharya and Karnik, 1996). These data indicate that BBP1 represents a novel protein containing a functional module shared with members of the G protein-coupled receptor superfamily. Specifically, it appears that BBP1 retains the critical DRF sequence between two predicted tm domains, so may have the potential to couple to a G protein regulated signaling pathway.

Figure 3:
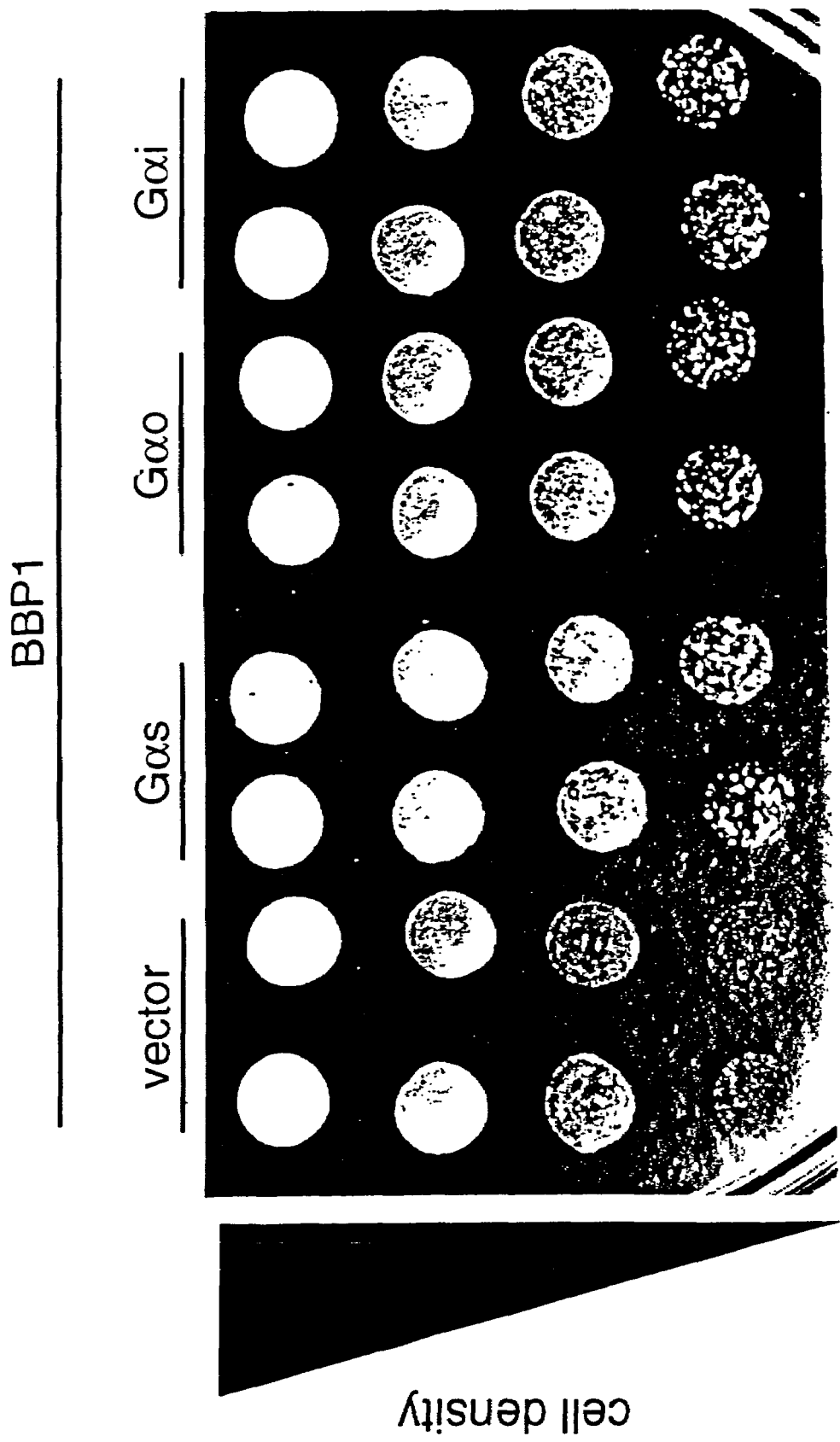
FIG. 3: Bioassays demonstrating BBP1 interactions with Gα proteins. The predicted intracellular domain of BBP1 was expressed as a Gal4 DNA-binding domain with portions of rat Gαs, Gαo, or Gαi2 expressed as Gal4 activation domain fusion proteins. Y2H responses of two independently derived clones of each strain were compared to responses of cells lacking a G protein component (vector). The protocol is as described in the legend to FIG. 2.

Structural analysis of BBP1 indicated it contained a structural motif known to be a Gα protein activating sequence in the related G protein-coupled receptors. Y2H assays demonstrating the interaction of BBP1 with various members of the G protein coupled receptors are illustrated in FIG. 3. Based on structural predictions, BBP1 is depicted as transversing a membrane twice with both termini in the lumenal compartment. Other orientations cannot be entirely ruled out. The potential protein interactions described above were investigated in Y2H assays. Two overlapping portions of the BBP1 sequences contained in the BBP1Δtm clone were amplified and cloned into the Y2H vector pACT2 (expression plasmids pEK216 and pEK219, Table 2 and corresponding proteins BBP1ΔN and BBP1ΔC, FIG. 4). The ΔC construct is lacking both tm domains; the ΔN construct encodes the first tm domain plus the preceding 52 amino acids. These fusion proteins were assayed with the BAP fusion protein and responses compared to those of strains expressing the larger BBP1Δtm protein. These results suggest that a major determinant for the association with BAP is contained within the BBP1 region predicted to be topographically similar to BAP in the wild-type APP protein.

Example 4

Tissue Distribution of Human BBP1 Expression

Figure 6:
FIG. 6: Expression of BBP1 and APP in cells of the hippocampus. Images of in situ hybridization autoradiograms showing the pattern of BBP1 (A) and APP (B) expression in human hippocampal and entorhinal cortex. The sections used to generate these images were taken from postmortem specimens obtained from two different patients. Abbreviations: DG=dentate gyrus; CA1=hippocampal subfield; EC=entorhinal cortex.
Figure 6:

Expression of BBP1 mRNA was evaluated as an initial step in elucidating the activity of the gene and its product. A major transcript of 1.25 kb was observed in all tissues (FIG. 5A). There was a high level of expression in heart. Whole brain exhibited an intermediate level of expression. Samples derived from separate brain regions all exhibited BBP1 expression (FIG. 5B). Interestingly, limbic regions contained relatively greater amounts of BBP1 mRNA. These are the regions of the brain where BAP aggregation and associated neurotoxicity initially occur. Analysis of in situ hybridization autoradiograms obtained using a BBP1-specific riboprobe indicated that in human hippocampus and entorhinal cortex, BBP1 mRNA is expressed in medium to large cells in a pattern consistent with expression in neurons as opposed to glial cells (FIG. 6). Moreover, BBP1 mRNA is expressed in virtually all hippocampal and entorhinal neurons, i.e., there do not appear to be any real or laminar differences in the intensity of the hybridization signal. Interestingly, the pattern of BBP1 expression was strikingly similar to the pattern observed using a riboprobe directed against mRNA for the amyloid precursor protein APP (FIG. 6). In summary, BBP1 mRNA was observed in all tissues and all brain regions examined. In situ analysis of BBP1 mRNA expression also revealed extensive expression in the hippocampus region.

Example 5

Cell Line Distribution of BBP1 Expression

BBP1 expression was also investigated in numerous cell lines and data were extracted from dbEST, the collection of expressed sequence tags from the National Center for Biotechnology Information. Reverse-transcription polymerase chain reaction (RT-PCR) methods were utilized to qualitatively assess BBP1 mRNA expression in cell lines commonly utilized for recombinant protein expression as well as a variety of cancer cell lines. BBP1 was observed in hamster CHO and human HEK293 cells. Signals were observed in the embryonic stem cell line Ntera-2 and neuroblastoma lines IMR32 and SK-N-SH. BBP1 expression was observed in cancer cell lines representing the following tissue origins: colon (Cx-1, Colo205, MIP101, SW948, CaCo, SW620, LS174T), ovarian (A2780S, A2780DDP), breast (MCF-7, SKBr-3, T47-D, B7474), lung (Lx-1, A5439), melanoma (Lox, Skmel30), leukemia (HL60, CEM), prostate (LNCAP, Du145, PC-3). A Northern blot probing mRNA isolated from the following cancer cell lines demonstrated BBP1 expression in all samples: promyelocytic leukemia (HL-60), carcinoma (HeLa S3), chronic myelogenous leukemia (K-562), lymphoblastic leukemia (MOLT-4), Burkitt's lymphoma (Raji), colorectal adenocarcinoma (SW480), lung carcinoma (A549), and melanoma (G361).

Example 6

Selective Interaction of BBP1 with Human BAP Versus Rodent BAP

There are three amino acid substitutions (G5R, F10Y and R13H) in the rodent BAP sequence compared to the human sequence. The rodent peptide demonstrated reduced neurotoxicity and an absence of binding to human brain homogenates (Maggio et al., 1992). It was of interest, therefore, to evaluate the association of rodent BAP with BBP1 in the Y2H system. The sequence of human BAP in pEK162 was changed to encode the rodent peptide by oligonucleotide directed mutagenesis by PCR, described above. The resultant plasmid, pEK240, was identical to the human BAP fusion protein expression plasmid utilized throughout the present invention except for the three codons producing the amino acid substitutions for the rodent peptide sequence. Interactions between BBP1 fusion protein and rodent and human BAP fusion proteins were compared by Y2H bioassay. Strains expressing BBP1 and the rodent BAP failed to produce a growth response (FIG. 7). This finding supports the premise that BBP1 may serve as a specific mediator of the neurotoxic effects of BAP, and provides a mechanism to explain the reduced neurotoxicity of the rodent BAP. Importantly, these data also serve to illustrate the high degree of specificity of the BBP1/BAP interaction in the Y2H assays since the substitution of three amino acids in BAP was sufficient to completely abrogate the association (FIG. 7).

Example 7

In Vitro Binding of Radiolabeled Beta-Amyloid Protein to BBP1 Protein

Initially, the novel gene product, BBP1, expressed from a fetal brain library as a fusion protein, was shown to interact with beta-amyloid protein (BAP), also expressed as a fusion protein via a yeast 2 hybrid system. To confirm these initial findings, the potential binding of beta-amyloid protein to full-length BBP1 protein was investigated in an in vitro radioligand binding assay. Specifically, radiolabeled human beta-amyloid protein (1–42) was shown to bind with in vitro synthesized myc-tagged BBP1 protein, as evidenced by the ability to co-precipitate beta-amyloid protein with tagged-BBP1 protein. The details of the radioligand binding assay are described below.

Protein A agarose bead+secondary antibody complexes were generated by incubating 2.5 µL ImmunoPurePlus immobilized Protein A (Pierce, Rockford, Ill.) with 10 mg AffiniPure rabbit a-mouse IgG (H+L) (Jackson ImmunoResearch Laboratories, Inc., West Grove, Pa.) in 50 mL cold low salt binding buffer (50 mM Tris pH7.6, 150 mM NaCl, 2 mM EDTA 1% IGEPAL, and protease inhibitors [5 µg/mL leupeptin, 5 µg/mL aprotinin, 2 µg/mL pepstatin A, 0.25 mMPMSF]) with rotation overnight at 4° C. The beads were washed 4x with 1 mL binding buffer and were resuspended in 1.25 mL binding buffer to give a 50% slurry. In some experiments, a 250 mL aliquot of this slurry was incubated in Superblock (Pierce) with rotation overnight at 4° C. The beads were washed 4x with 1 mL Superblock and resuspended in 125 µL Superblock.

The DNA template for in vitro transcription/translation of the BBP1 protein, including a Kozak consensus sequence and sequences encoding a myc epitope, EQKLISEEDL, directly upstream of the first methionine of BBP1 coding region, was inserted into the BamHI/EcoRI sites of pSP64polyA vector (Promega, Madison, Wis.). The DNA template was, in part, PCR generated, utilizing the forward primer, 5' GCAGGATCCCCACCATGGAGCAGAAGCT-GATCAGCGAGGAGGACCTGCATAT TTTAAAAGGGTCTCCCAATGTGA 3' (SEQ ID NO:31) and reverse primer, 5' TCACGGCCTCCGGAGCAGACGG 3' (SEQ ID NO:32) and PFU polymerase, according to the manufacturer's conditions (Stratagene, La Jolla, Calif.). The PCR cycling conditions were an initial denaturing step at 95° C. for 3 min, 30 cycles of denaturation at 94° C. for 30 sec, annealing at 65° C. for 30 sec, elongation at 72° C. for 1 min 30 sec, and followed by a final elongation at 72° C. for 5 min. The amplicon was digested with BamHI+NotI and ligated to the 3' end of BBP1, housed on a NotI/EcoRI fragment, which had been previously gel purified from the recombinant expression cassette.

Approximately 2.54 µCi of disaggregated [Krishnamurthy, K. et al. (1998). Characterization of fibrillogenesis of amyloid peptide. Abstracts of the American Chemical Society, vol., p., 215$^{th}$ National Meeting and Exposition, Mar. 29–Apr. 2, 1998, Dallas, Tx.] human [$^{125}$I]-Tyr-Ab$_{1-42}$) (American Radiolabeled Chemicals, Inc., St.

Louis, Mo.) was incubated with 5–10 mL of N-terminal c-myc tagged human BBP1 (⅕–¹⁄₁₀ reaction volume obtained using the TNT SP6 Coupled Reticulocyte Lysate System [Promega, Madison, Wis.]) with rotation for ~6 hrs at 4° C. in a final volume of 1 mL cold low salt binding buffer (see above). Two micrograms of mouse a-myc and 25 mL of the Agarose protein A/rabbit a-mouse IgG complex (see above) were added to the reaction tube and incubated at 4° C. overnight with rotation. Immune complexes were washed 4x with 1 mL binding buffer and resuspended in 25 mL 2x Tricine loading dye (Novex, San Diego, Calif.) containing 5% b-Mercaptoethanol. Samples were boiled for 5 minutes and immediately placed on ice for 15 minutes. The tubes were briefly spun at 2500xg and the supernatant loaded on a 16% Tricine polyacrylamide gel (Novex, San Diego, Calif.) which was run at 50 mA for ˜90 min. The gel was soaked for 15 min in a drying solution composed of 20% acetic acid/10% methanol and dried at 80° C. for 1 hr under vacuum. The dried gel was subjected overnight to a phosphoimager screen which was scanned for analysis with the Storm phosphoimager (Molecular Dynamics, Sunnyvale, Calif.).

Figure 8:
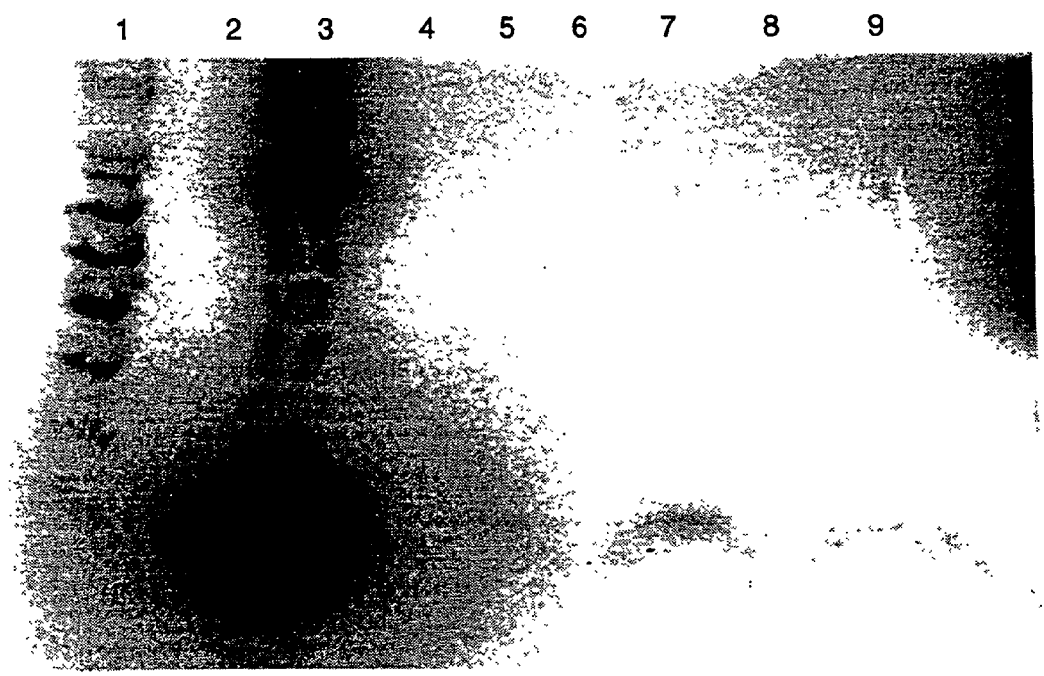
FIG. 8: In vitro BBP1 binding to beta-amyloid protein (1–42). In vitro transcribed and translated N-terminally myc-tagged BBP1 (~20 ng) was incubated with disaggregated human $[^{125}I]$-Tyr-BAP$_{(1-42)}$. The myc-tagged BBP1 was immunoprecipitated with mouse anti-myc antibody and rabbit anti-mouse IgG antibody conjugated to protein A-Agarose beads. lane 1, MW markers; lane 2, 4, 6, 8: blank; lane 3: $[^{125}I]$-Tyr-BAP$_{(1-42)}$ (disaggregated; ≈25 nCi); lane 5: Pre-incubation of rabbit anti-mouse IgG antibody conjugated to protein A-Agarose beads in Superblock, plus anti-myc antibody and radiolabeled BAP (no BBP1); lane 7: Pre-incubation of rabbit anti-mouse IgG antibody conjugated to protein A-Agarose beads in low salt binding buffer (see Material and Methods), plus mouse anti-myc antibody and radiolabeled BAP (no BBP1); lane 9: Pre-incubation of rabbit anti-mouse IgG antibody conjugated to protein A-Agarose beads in Superblock, plus mouse anti-myc antibody, radiolabeled BAP, and in vitro synthesized myc-tagged BBP1.

Initial experiments attempting to co-immunoprecipitate radiolabeled BAP with myc-tagged BBP1 resulted in non-specific binding of BAP when agarose protein A/secondary antibody complexes were prepared in low salt binding buffer, even in samples lacking BBP1 (see FIG. 8, lane 7). To reduce these non-specific interactions, the agarose protein A/rabbit a-mouse IgG was incubated/washed in blocking reagent prior to binding, as outlined above. This blocking procedure reduced non-specific Ab binding to near zero when all immunoprecipitation components were available except myc-tagged BBP1 (FIG. 8, lane 5). Radiolabeled human BAP $_{(1-42)}$ was able to complex with in vitro transcribed/translated myc-tagged human BBP1 after immunoprecipitating myc-tagged BBP1 with anti-myc antibody (FIG. 8, lane 9), as seen by a band consistent in size with Ab (FIG. 8, lane 3). These data are consistent with human BAP binding to myc-tagged human BBP1 in vitro and support the initial observation that BAP interacts with BBP1 in a yeast two-hybrid system.

Example 8

Expression of Recombinant BBP1 Sensitizes Ntera2 Stem Cells to β-Amyloid Peptide A cultured cell system was utilized to investigate the effects of BBP1 expression on cellular sensitivity to BAP toxicity. Human Ntera-2 (Nt2) stem cells can be induced to differentiate into neuron-like cells (P. Andrews, Dev. Biol. 103:285–293, 1984). In that state, the cells exhibit a vulnerability to BAP that is similar in degree to that observed in primary neurons. Neurons affected by BAP exhibit characteristics of apoptosis before dying (see C. Cotman and A. Anderson, Mol. Neurobiol. 10:19–45, 1995). An early indicator of apoptosis, namely, condensation of chromatin, was used as an indicator for cellular responses to BAP. The undifferentiated stem cells did not exhibit significant sensitivity under the experimental conditions used in these studies. However, Nt2 stem cells transfected with a BBP1 expression plasmid became markedly sensitive to applied BAP, supporting the premise that BBP1 may act as a mediator of the toxic effects of β-amyloid peptide. The details of the experiment are below.

BBP cDNAs were modified by polymerase chain reaction (PCR) for expression from the vector pcDNA3.1 (Invitrogen Corp., Carlsbad, Calif.). BBP1 cDNA was amplified from pBBP1-fl, adding a 5' EcoRI and a 3' SalI site for cloning. The PCR primers were 5'-TGGTGAATTC GAAAGT-GTCG GTCTCCAAG ATG G (+strand) (SEQ ID NO:33) and 5'-CTTCGTCGAC TTA TGG ATA TAA TTG CGT TTT TC (−strand) (SEQ ID NO:34). The PCR product was digested with EcoRI+SalI and cloned into pcDNA3.1/EcoRI-XhoI to create pOZ363. Mutation of the arginine codon within the 'DRF' motif of the BBP1 cDNA was performed using the QuickChange system (Stratagene Co., La Jolla, Calif.). Oligonucleotides were synthesized and purified by Genosys Biotechnologies, Inc. (The Woodlands, Tex.). The R138 codon of BBP1 in pOZ363 was changed to a glutamate codon using the oligonucleotide 5'-GG TTG GGA GCA GAT GAA TTT TAC CTT GGA TAC CC (SEQ ID NO:35) and its exact reverse complement.

Human Ntera2 (Nt2) stem cells were maintained in Dulbecco's Modified Eagle's medium (high glucose) supplemented with 10% fetal bovine serum. Retinoic acid was utilized to differentiate cells to a neuronal phenotype as described by P. Andrews (Dev. Biol. 103:285–293, 1984). Expression constructs were introduced into stem cells by electroporation. The cells were split 1:2 the day before electroporation to ensure exponential growth for maximal survival and efficiency. On the day of electroporation the cells were treated with trypsin and washed two times in phosphate buffered saline (PBS). They were resuspended at $1.3 \times 10^7$ cells per 0.3 ml in RPMI 1640 with 10 mM dextrose and 0.1 mM dithiothriotol. DNA amounts were 7.5 mg subject DNA with 2.5 mg pEGFP-N1 (CLONTECH Laboratories, Palo Alto, Calif.) to monitor transfection. Cells were pre-incubated for 10 mins on ice with DNA, pulsed, and post-incubated for 10 min on ice. A GenePulser instrument (BioRad Corp., Hercules, Calif.) was utilized with a cuvette gap of 0.4 cm, voltage of 0.24 kV, and capacitance of 960 mF. Cells were plated in standard 24-well plates. Approximately 24 hrs after transfection, growth medium was replaced with medium containing the indicated concentration of BAP. After incubation for 44 to 48 hrs, the chromatin-specific dye Hoechst 33342 (Molecular Probes, Inc., Eugene, Oreg.) was added to a concentration of 10 ng/ml. Medium was removed after 10 min and cells were washed with PBS. Cells were then fixed by immersion in PBS containing 4% paraformaldehyde.

Forty-residue β-amyloid peptide was obtained from AnaSpec, Inc., San Jose, Calif. Peptide was dissolved and stored in hexafluoro-isopropanol at 1 mg/ml. Peptide was lyophilized by pervasion with nitrogen, then resuspended in 1.155 ml cell growth medium and divided into 0.13 ml aliquots in a 96-well plate. The plate was shaken at 500 rpm for 4 hrs. Samples were then combined and normalized to a final BAP concentration of 50 mM. The same preparation of aggregated (or aged) BAP utilized in the described experiments was also shown to be toxic to primary hippocampal neurons. Forty-two residue β-amyloid peptide was obtained from Bachem Bioscience Inc. It was dissolved directly in cell growth medium and added to experimental samples. This preparation had no discernible effect on differentiated Nt2 neurons.

Cells were visualized on a Zeiss Axiovert fluorescent microscope fitted with dichroic filters as follows. Hoechst dye visualization utilized excitation at 330 microns, emission at 450; EGFP visualization with excitation at 475, emission at 535. A minimum of 60 transfected (EGFP+) cells were scored per sample.

β-amyloid peptide exhibited substantial neurotoxicity in culture only after aging to produce fibrillar aggregates. Peptide freshly dissolved in media showed reduced potency. To investigate potential BBP1 effects on BAP-mediated toxicity, Nt2 stem cells were transfected with pEGFP or with pEGFP plus the BBP1 expression plasmid pOZ363 as described.

Figure 9:
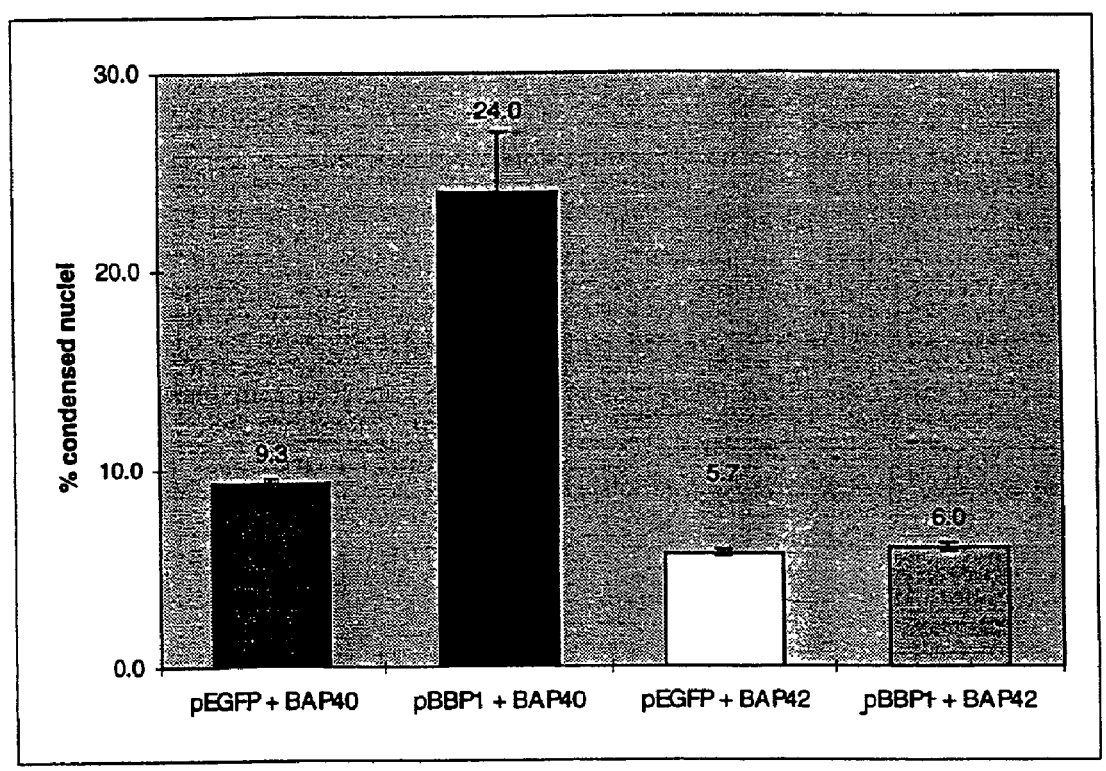
FIG. 9: Effect of BBP1 on Nt2 Stem Cells Exposed to BAP. Nt2 neurons, and Nt2 stem cells transfected with pEGFP alone or cotransfected with pEGFP plus pBBP1 (also referred to as pOZ363), were treated for 48 hrs with aged (toxic) or fresh (nontoxic) BAP preparations as described in the text. Final concentrations were 2 μM or 5 μM, respectively. Cells were prepared for determinations of nuclear morphology as described. Values represent the mean percent condensed nuclei, derived from viewing multiple fields for each sample. For the stem cell populations, only transfected cells (EGFP+) were scored.
Figure 10:
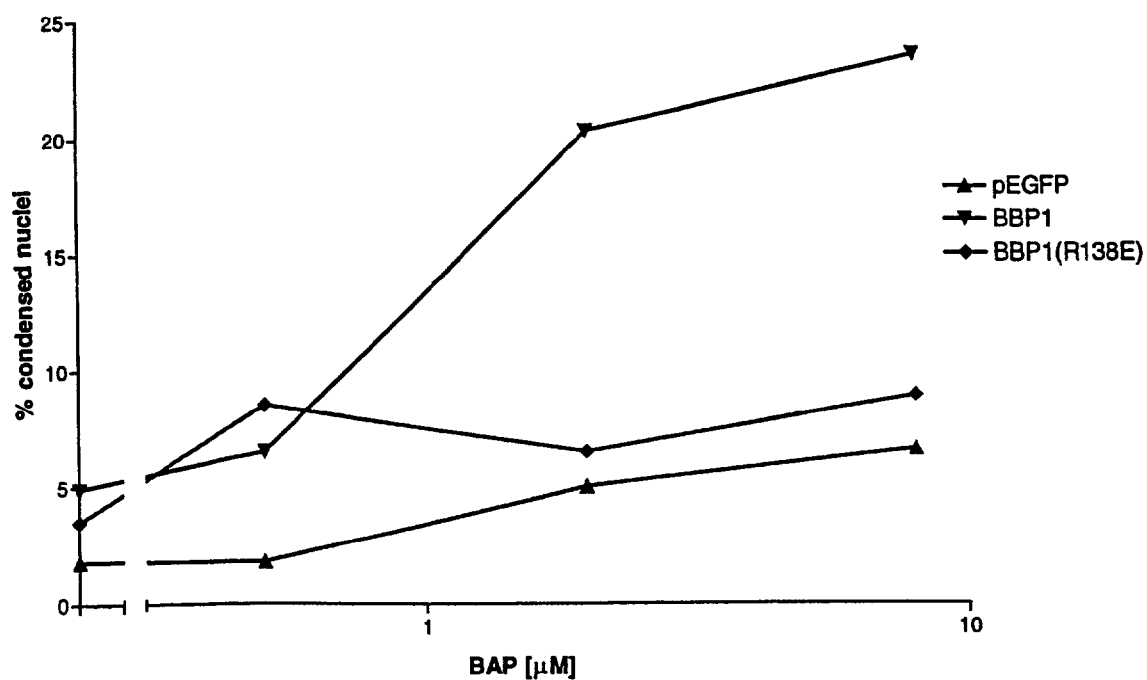
FIG. 10. Sensitivity of Nt2 stem cells to modified BBP. Nt2 stem cells were transfected with pEGFP alone or cotransfected with pEGFP plus BBP1 or BBP1(R138E)

These samples were treated with aged (toxic) or fresh (nontoxic) BAP as described above. Nt2 neurons, which exhibited a much greater sensitivity to BAP then the undifferentiated stem cells, were treated at the same time to assess toxicity of the BAP preparations. After treatment for 48 hours, the chromatin of cells was stained with Hoechst dye to reveal nuclear structure and the cells were then fixed. The neurons treated with aged BAP exhibited a marked increase in condensed nuclei compared to those treated with the fresh BAP (FIG. 9), confirming the respective toxicity of the two preparations. In contrast to the observations with Nt2 neurons, the stem cell controls exhibited only a small (not statistically significant) response to the toxic BAP (pEGFP; FIG. 9). However, transfection of the cells with the BBP1 expression plasmid resulted in significant ($P<0.001$, Yates modified chi-squared test) increase in the frequency of condensed nuclei (FIG. 9). Importantly, the nontoxic preparation of BAP had no effect in the assay (FIG. 9), establishing that the BBP1-mediated response in these assays is specific for formulations of BAP that are also toxic to Nt2 neurons, and suggesting a correlation between BBP1 and the mechanism of BAP toxicity. In a similar experiment, the toxic BAP was added to transfected Nt2 stem cells at varying concentrations (0, 0.5, 2, or 8 micromolar). Again, cells transfected with pEGFP alone exhibited no significant response to BAP treatment (FIG. 10). In contrast, cells transfected with a BBP1 expression plasmid demonstrated a substantial, significant ($P<0.005$), and dose-dependent sensitivity to the toxic BAP (FIG. 10).

It was predicted that the BBP1 protein might modulate the activity of heterotrimeric G proteins based on its structural relationship to known G protein-coupled receptors and the demonstration that its predicted cytosolic loop can associate with Gα proteins in a yeast 2-hybrd assay (Example 3, FIG. 3). It has been shown that substitution of the conserved arginine residue in the 'DRF' motif of 7-transmembrane domain G protein-coupled receptors attenuates their activity (E. Burstein, T. Spalding, and M. Brann, J. Biol. Chem. 273:24322–24327, 1998; W. Rosenthal et al., J. Biol. Chem. 268:13030–13033, 1993), and that substitution to glutamate (E) can completely eliminate agonist-mediated activation of G protein (P. Jones, C. Curtis, and E. Hulme, Eur. J. Pharmacol. 288:251–257, 1995). The BBP1 arginine-138 codon was mutated to a codon for glutamate and this BBP1 variant was examined for induction of sensitivity to BAP. This single amino acid substitution abrogated the effects of BBP1 (FIG. 10), suggesting that the BAP sensitization affected by BBP1 in this system may be mediated through a G protein pathway.

It is clear that the invention may be practiced otherwise than as particularly described in the foregoing description and examples. Numerous modifications and variations of the present invention are possible in light of the above teachings and therefore are within the scope of the appended claims.

REFERENCES

Acharya, S., and Karnik, S. (1996). Modulation of GDP release from transducin by the conserved Glu134-Arg135 sequence in rhodopsin. J Biol Chem 271, 25406–25411.

Altschul, Gish, W., Miller, W., Myers, E., and Lipman, D. (1990). Basic local alignment search tool. J Mol Biol 215, 403–410.

Chartier-Harlin, M., Crawford F., Houlden, H., Warren, A., Hughes, D., Fidani, L., Goate, A., Rossor, M., Roques, P., Hardy, J., and Mullan, M. (1991). Early-onset Alzheimer's disease caused by mutations at codon 717 of the β-amyloid precursor protein gene. Nature 353, 844–846.

DuYan, S., Chen, X., Fu, J., Chen, M., Zhu, H., Roher, A., Slattery, T., Zhao, L., Nagashima, M., Morser, J., Migheli, A., Nawroth, P., Stern, D., and Schmidt, A. (1996). RAGE and amyloid-β peptide neurotoxicity in Alzheimer's disease. Nature 382, 685–691.

El Khoury, J., Hickman, S., Thomas, C., Cao, L., Silverstein, S., and Loike, J. (1996). Scavenger receptor-mediated adhesion of microglia to β-amyloid fibrils. Nature 382, 716–719.

Goate, A., Chartier-Harlin, M., Mullan, M., Brown, J., Crawford, F., Fidani, L., Giuffra, L., Haynes, A., Irving, N., James, L., Mant, R., Newton, P., Rooke, K., Roques, P., Talbot, C., Pericak-Vance, M., Roses, A., Williamson, R., Rossor, M., Owen, M., and Hardy, J. (1991). Segregation of a missense mutation in the amyloid precursor protein gene with familial Alzheimer's disease. Nature 349, 704–706.

Hendriks, L., van Dujin, C., Cras, P., Cruts, M., van Hul, W., van Harskamp, F., Martin, J.-J., Hofman, A., and van Broeckhoven, C. (1992). Presenile dementia and cerebral haemorrhage linked to a mutation at codon 692 of the β-amyloid precursor protein gene. Nat Genet 1, 218–221.

Jacobsen, J., Spruyt, M., Brown, A., Sahasrabudhe, S., Blume, A., Vitek, M., Muenkel, H., and Sonnenberg-Reines, J. (1994). The release of Alzheimer's disease β amyloid peptide is reduced by phorbol treatment. J. Biol Chem 269, 8376–8382.

Jacobsen, J, Muenkel, H, Blume, A, and Vitek, M (1991). A novel species-specific RNA related to alternatively spliced amyloid precursor protein mRNAs. Neurobiol of Aging 12, 575–583.

Kang, Y.-S., Kane, J., Kurjan, J., Stadel, J., and Tipper, D. (1990). Effects of expression of mammalian Gα and hybrid mammalian-yeast Gα proteins on the yeast pheromone response signal transduction pathway. Mol Cell Biol 10, 2582–2590.

LaFerla, F., Tinkle, B. Bieberich, C. Haudenschild, C., and Jay, G. (1995). The Alzheimer's Aβ peptide induces neurodegeneration and apoptotic cell death in transgenic mice. Nature Genetics 9, 21–30.

Lassmann, H., Bancher, C., Breitschopf, H., Wegiel, J., Bobinski, M., Jellinger, K., and Wisniewski, H. (1995). Cell death in Alzheimer's disease evaluated by DNA fragmentation in situ. Acta Neuropathol 89, 35–41.

Levy, E., Carman., Fernandez-Madrid, I., Power, M., Leiberburg, I., vanDuinen, S., Bots, G., Luyendijk, W., and Frangione, B. (1990). Mutation of the Alzheimer's disease amyloid gene in hereditary cerebral hemorrhage, Dutch type. Science 248, 1124–1126.

Loo, D., Copani, A., Pike, C., Whittemore, E., Walencewicz, A., and Cotman, C. (1993). Apoptosis is induced by β-amyloid in cultured central nervous system neurons. Proc Natl Acad Sci USA 90, 7951–7955.

Maggio, J., Stimson, E., Ghilardi, J., Allen, C., Dahl, C., Whitcomb, D., Vigna, S., Vinters, H., Labenski, M., and Mantyh, P. (1992). Reversible in vitro growth of Alzheimer disease β-amyloid plaques by deposition of labeled amyloid peptide. Proc Natl Acad Sci USA 89, 5462–5466.

Mullan, M., Crawford, F., Axelman, K., Houlden, H., Lilius, L., Winblad, W., and Lannfelt, L. (1992). A pathogenic mutation for probably Alzheimer's disease in the N-terminus of β-amyloid. Nat Genet 1, 345–347.

Murrell, J., Farlow, M., Ghetti, B., and Benson, M. (1991). A mutation in the amyloid precursor protein associated with hereditary Alzheimer disease. Science 254, 97–99.

Nishimoto, I., Okamoto, T., Matsuura, Y., Takahashi, S., Okamoto, T., Murayama, Y., and Ogata, E. (1993). Alzheimer amyloid protein precursor complexes with brain GTP-binding protein Go. Nature 362, 75–79.

Ozenberger, B., and Young, K. (1995). Functional interaction of ligands and receptors of the hematopoietic superfamily in yeast. Mol Endocrinol 9, 1321–1329.

Rhodes K., Monaghan M., Barrezueta N., Nawoschik S., Bekele-Arcuri Z., Matos M., Nakahira K., Schechter L., and Trimmer J. (1996). Voltage-gated K+ channel beta subunits: expression and distribution of Kv beta 1 and Kv beta 2 in adult rat brain. J Neurosci 16, 4846–4860.

Scheuner, D., Eckman, C., Jensen, M., Song, X., Citron, M., Suzuki, N., Bird, T., Hardy, J., Hutton, M., Kukull, W., Larson, E., Levy-Lahad, E., Viitanen, M., Peskind, E., Poorkaj, P., Schellenberg, G., Tanzi, R., Wasco, W., Lannfelt, L., Selkoe, D., and Younkin, S. (1996). Aβ42(43) is increased in vivo by the PS ½ and APP mutations linked to familial Alzheimer's disease. Nat Med 2, 864–870.

Selkoe, D. (1997). Alzheimer's Disease: Genotypes, phenotype, and treatments. Science 275, 630–631.

Smale, G., Nichols, N., Brady, D., Finch, C., and Jr, W. H. (1995). Evidence for apoptotic cell death in Alzheimer's disease. Exp Neurol 133, 225–230.

Tanzi, R., Gusella, J., Watkins, P., Bruns, G., George-Hyslop, P. S., vanKeuren, M., Patterson, D., Pagan, S., Kurnit, D., and Neve, R. (1987). Amyloid β protein gene: cDNA, mRNA distribution and genetic linkage near the Alzheimer locus. Science 235, 880–884.

Tatusov, R., Altschul, S., and Koonin, E. (1994). Detection of conserved segments in proteins: Iterative scanning of sequence databases with alignment blocks. Proc Natl Acad Sci USA 91, 12091–12095.

Wade Harper, J., Adami, G. R., Wei, N., Keyomarsi, K., and Elledge, S. J. (1993). The p21 Cdk-interacting protein Cip1 is a potent inhibitor of G1 cyclin-dependent kinases. Cell 75, 805–816.

Watt, J., Pike, C., Walencewicz-Wasserman, A., and Cotman, C. (1994). Ultrastructural analysis of β-amyloid-induced apoptosis in cultured hippocampal neurons. Brain Res 661, 147–156.

Yamatsuji, T., Matsui, T., Okamoto, T., Komatsuzaki, K., Takeda, S., Fukumoto, H., Iwatsubo, T., Suzuki, N., Asami-Odaka, A., Ireland, S., Kinane, T., Giambarella, U., and Nishimoto, I. (1996). G. protein-mediated neuronal DNA fragmentation induced by familial Alzheimer's Disease-binding mutants of APP. Science 272, 1349–1352.

Yan, S., Fu, J., Soto, C., Chen, X., Zhu, H., Al-Mohanna, F., Collison, K., Zhu, A., Stern, E., Saido, T., Tohyama, M., Ogawa, S., Roher, A., and Stern, D. (1997). An intracellular protein that binds amlyoid-β peptide and mediates neurotoxicity in Alzheimer's disease. Nature 389, 689–695.

---

What is claimed is:

1. An isolated, recombinant or chemically synthesized polynucleotide encoding a protein comprising the amino acid sequence of SEQ ID NO: 2.

2. An isolated, recombinant or chemically synthesized polynucleotide encoding a protein comprising a fragment of the amino acid sequence of SEQ ID NO: 2 having human β-amyloid peptide binding activity, the fragment comprising the amino acid sequence from amino acid 68 to amino acid 269 of SEQ ID NO: 2.

3. An isolated, recombinant or chemically synthesized polynucleotide encoding a peptide comprising the amino acid sequence of SEQ ID NO: 2 from amino acid 1 to amino acid 67.

4. An isolated, recombinant or chemically synthesized polynucleotide according to claim 3 wherein the sequence is the nucleotide sequence of SEQ ID NO: 1 from nucleotide 1 to nucleotide 201.

5. A probe or primer comprising the nucleotide sequence of nucleotides 157–201 of SEQ ID NO: 1.

6. A probe or primer comprising the nucleotide sequence of nucleotides 172–194 of SEQ ID NO: 1.

7. An isolated, recombinant or chemically synthesized polynucleotide comprising at least one expression control sequence operably linked to at least one polynucleotide selected from the group consisting of the polynucleotide of claim 1 and the polynucleotide of claim 2.

8. An isolated host cell transformed with the polynucleotide of claim 7.

9. The isolated host cell of claim 8 wherein said cell is a prokaryotic or eukaryotic cell.

10. An isolated, recombinant or chemically synthesized polynucleotide comprising a nucleic acid sequence encoding amino acids 185–217 of SEQ ID NO:2, or the full complement of said nucleic acid sequence.

11. An expression vector comprising the polynucleotide of claim 10.

12. An isolated, recombinant or chemically synthesized polynucleotide comprising a nucleic acid sequence or the full complement thereof, wherein said nucleic acid sequence encodes amino acids 123–202 of SEQ ID NO:2 with an arginine to glutamate substitution at residue 200.

13. The polynucleotide of claim 12, wherein said nucleic acid sequence encodes amino acids 68–269 of SEQ ID NO:2 with said arginine to glutamate substitution at residue 200.

14. An expression vector comprising the polynucleotide of claim 12.

15. An isolated, recombinant or chemically synthesized polynucleotide capable of hybridizing under a stringency condition to a nucleic acid sequence or the full complement thereof, wherein said nucleic acid sequence consists of SEQ ID NO:1, and wherein said stringency condition is selected from the group consisting of conditions A, C, E, G, I, K, M, O, and Q of Table 1, and the length of said polynucleotide is at least 75% of that of SEQ ID NO:1.

16. The polynucleotide of claim 15 wherein said stringency condition is selected from the group consisting of conditions A, C, E, G, I, and K of Table 1.

17. The polynucleotide of claim 15 wherein said stringency condition is selected from the group consisting of conditions A, C, and E of Table 1.

18. A recombinant vector comprising the polynucleotide of claim 15.

19. The polynucleotide of claim 1 wherein said polynucleotide comprises SEQ ID NO:1.

20. The polynucleotide of claim 2 wherein said polynucleotide comprises nucleotides 202–807 of SEQ ID NO:1.

21. An expression vector comprising an expression control sequence operably linked the polynucleotide of claim 10.

22. The polynucleotide of claim 12 wherein said nucleic acid sequence encodes amino acids 63–269 of SEQ ID NO:2 with said arginine to glutamate substitution at residue 200 in SEQ ID NO:2.

23. An isolated, recombinant or chemically synthesized polynucleotide comprising a nucleic acid sequence encoding a β-amyloid peptide-binding protein encoded by the cDNA insert of clone BBP1-fl deposited under accession number ATCC 98617.

24. The polynucleotide of claim 23 wherein said nucleic acid sequence comprises the cDNA insert of clone BBP1-fl deposited under accession number ATCC 98617.

25. An expression vector comprising an expression control sequence operably linked to the polynucleotide of claim 23.

26. An isolated host cell comprising the expression vector of claim 25.

27. An isolated, recombinant or chemically synthesized polynucleotide comprising a nucleic acid sequence encoding a β-amyloid peptide-binding protein encoded by the cDNA insert of clone pEK196 deposited under accession number ATCC 98399.

28. The polynucleotide of claim 27 wherein said nucleic acid sequence comprises the cDNA insert of clone pEK196 deposited under accession number ATCC 98399.

29. An expression vector comprising an expression control sequence operably linked to the polynucleotide of claim 27.

30. An isolated host cell comprising the expression vector of claim 29.

* * * * *

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (xi) SEQUENCE DESCRIPTION: SEQ ID NO: 1:

GTGTGAGGAA CGGGAAATTC ATCGAAGGAC ATCCCCCGAC          40

(2) INFORMATION FOR SEQ ID NO: 2:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (xi) SEQUENCE DESCRIPTION: SEQ ID NO: 2:

GGAAGGTCGA TGTCTAGTTA ATCGAAGGAC ATCCCCCGAC          40

(2) INFORMATION FOR SEQ ID NO: 3:

(i) SEQUENCE CHARACTERISTICS:
      (A) LENGTH: 18 amino acids
      (B) TYPE: amino acid
      (D) TOPOLOGY: linear (ii) MOLECULE TYPE: peptide (iii) HYPOTHETICAL: NO (xi) SEQUENCE DESCRIPTION: SEQ ID NO: 3:

Ser Val Leu Thr Leu Thr Asn Leu Thr Gly Leu Asp Thr Gly Glu Tyr
1           5                  10              15

Phe Cys